(12) United States Patent
Hermans et al.

(10) Patent No.: US 9,040,666 B2
(45) Date of Patent: May 26, 2015

(54) SINGLE-DOMAIN ANTIGEN-BINDING PROTEINS THAT BIND MAMMALIAN IGG

(75) Inventors: Wilhelmus Josephus Johanna Hermans, Oud-Gastel (NL); Sandra Bezemer, Schiedam (NL); Yvonne Mathalie Mijnsbergen, Nieuwdorp (NL)

(73) Assignee: BAC IP B.V., Naarden (NL)

( * ) Notice: Subject to any disclaimer, the term of this patent is extended or adjusted under 35 U.S.C. 154(b) by 587 days.

(21) Appl. No.: 12/669,034

(22) PCT Filed: Jul. 8, 2008

(86) PCT No.: PCT/NL2008/050460
§ 371 (c)(1),
(2), (4) Date: Mar. 30, 2010

(87) PCT Pub. No.: WO2009/011572
PCT Pub. Date: Jan. 22, 2009

(65) Prior Publication Data
US 2010/0311119 A1 Dec. 9, 2010

Related U.S. Application Data

(60) Provisional application No. 60/949,557, filed on Jul. 13, 2007.

(30) Foreign Application Priority Data

Jul. 13, 2007 (EP) .................................. 07112456
Oct. 30, 2007 (EP) .................................. 07119634

(51) Int. Cl.
C07K 16/00 (2006.01)
C12P 21/08 (2006.01)
C07K 16/42 (2006.01)
C07K 1/00 (2006.01)

(52) U.S. Cl.
CPC ......... C07K 16/4283 (2013.01); *C07K 2317/22* (2013.01); *C07K 2317/33* (2013.01); *C07K 2317/569* (2013.01); *C07K 2317/92* (2013.01); *C07K 2317/94* (2013.01)

(58) Field of Classification Search
None
See application file for complete search history.

(56) References Cited

U.S. PATENT DOCUMENTS

2005/0095726 A1  5/2005  Fang et al.

FOREIGN PATENT DOCUMENTS

| EP | 1 693 384 | 8/2006 |
|----|-----------|--------|
| WO | WO 98/12349 | 3/1998 |
| WO | WO 01/44301 | 6/2001 |
| WO | WO 02/48193 | 6/2002 |
| WO | WO 2005/113604 | 12/2005 |
| WO | WO 2006/059904 | 6/2006 |

OTHER PUBLICATIONS

De Genst et al. Developmental and Comparative Immunology 30(2006) 187-198.*
Tereshko et al. Protein Science (2008) 17:1175-1187.*
Deschacht et al. The Journal of Immunology, 2010, 184:5696-5704.*
Sircar et al. The Journal of Immunology 2011, 186:6357-6367.*
Examiner Written Description Training Materials. Revision 1, Mar. 25, 2008. pp. 1-84.*
Klooster, et al., "Improved Anti-IgG and HSA Affinity Ligands: Clinical Application of VHH Antibody Technology", Journal of Immunological Methods, 324, pp. 1-12, 2007.
Haaft, et al., "Separations in Proteomics: Use of Camelid Antibody Fragments . . . ", http://www.captureselect.com/downloads/separations-in-protemics.pdf, pp. 29-40, 2005.
Hermans, et al., "Implementation of Novel Affinity . . . ", Downstream-Cap '05, http://www.gelifesciences.co.jp/newsletter/downstream/pdf/cap05_abstracts.pdf, pp. 9-11, 2005.
Chevrier, et al., Sensitive Detection of Human IgG in ELISA Using a Monoclonal Anti-IgG-Peroxidase . . . , Hybridoma and Hybridomics, 23, pp. 362-367, 2004.

* cited by examiner

*Primary Examiner* — Chun Dahle

(57) ABSTRACT

The present application relates to antigen-binding proteins that are capable of binding to mammalian IgG. The framework regions of the antigen-binding proteins of the application preferably correspond to those of antibodies naturally that are devoid of light chains as may e.g. be found in camelids. The application further relates to nucleic acids that encode such antigen-binding proteins, to immunoadsorbent materials that comprise such proteins, to the uses of such immunoadsorbent materials for the purification of mammalian IgG antibodies and for therapeutic apheresis.

8 Claims, 1 Drawing Sheet

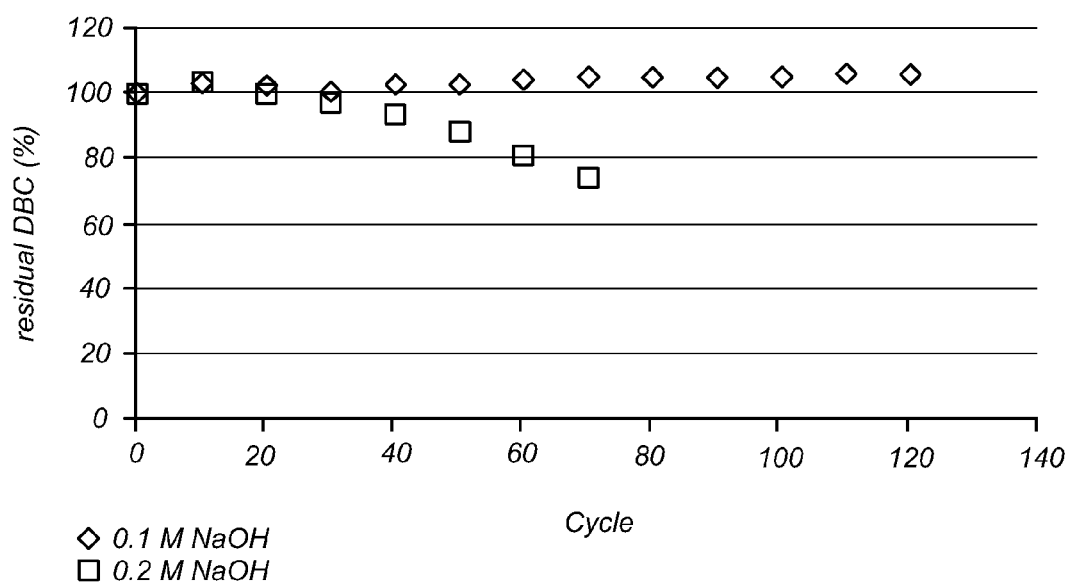

SINGLE-DOMAIN ANTIGEN-BINDING PROTEINS THAT BIND MAMMALIAN IGG

RELATED APPLICATIONS

The present application is a U.S. National Phase Application of International Application No. PCT/NL2008/050460, filed Jul. 8, 2008, which claims the benefit of European Patent Application No. 07112456.4, filed Jul. 13, 2007; U.S. Provisional Application No. 60/949,557, filed Jul. 13, 2007; and European Patent Application No. 07119634.9, filed Oct. 30, 2007, all of which are hereby incorporated by reference in their entireties.

SEQUENCE LISTING SUBMISSION VIA EFS-WEB

A computer readable text file, entitled "067131-5020-SequenceListing.txt," created on or about Aug. 18, 2010 with a file size of about 83 kb contains the sequence listing for this application and is hereby incorporated by reference in its entirety.

FIELD OF THE INVENTION

The present invention relates to the field of biochemistry, in particular immunoglobulin purification and antibody technology. The invention relates to amino acid sequences that are capable of binding to mammalian IgG; to proteins and polypeptides comprising or essentially consisting of such amino acid sequences; to nucleic acids that encode such amino acid sequences, proteins or polypeptides; to immunoadsorbent materials that comprise such proteins and polypeptides; and to uses of such immunoadsorbent materials for the purification of mammalian IgG antibodies.

BACKGROUND OF THE INVENTION

Efficient, rapid, save and cost efficient purification of mammalian IgG antibodies, in particular human and/or humanized IgG antibodies is a much studied problem in the art. With the advent of new antibody based medicaments, purification of IgG becomes a more and more critical and costly step in the production of antibody based medicaments, requiring a high degree of purity. In addition, such antibodies must retain binding affinity and biological activities like effector functions.

For the purification of mammalian IgG antibodies, in particular human IgG or humanized IgG antibodies, commonly used purification methods comprise the use of classical biochemical separation and purification techniques such as anion/kation exchange, size-exclusion/gelfiltration, precipitations and use of specific affinity ligands. Commonly used ligands are bacterially derived proteins, Protein-A and Protein-G. Alternatively, Protein L can be used, but only for those immunoglobulins comprising a kappa light chain since Protein L does not bind lambda light chains.

Protein-A is a bacterial surface protein expressed by *Staphylococcus aureus*. Protein-A primarily recognizes a common site at the interface between $C_H2$ and $C_H3$ domains on the Fc part of human IgG1, IgG2 and IgG4 antibodies (Fey). In addition, Protein-A also shows binding to 12% of mouse and 50% of human $V_H$ domains (human $V_H$-III subclass). Although these latter interactions have a lower affinity (±200 nM for $V_H$ compared to <1 nM for e.g. human IgG1) Protein-A can be used for purification of Fab—and (sc)Fv fragments (independent of the Ig isotype). Protein-A, like Protein L acts as a superantigen on human B lymphocytes, probably induced by its $V_H$-III reactivity. Therefore, if the purified IgG antibodies are intended for therapeutic usage, a major safety concern is the possible presence of Protein-A in the purified therapeutic product as a result from the unintended detachment of Protein-A from its support material during the purification process (Protein-A leakage). Numerous publications link Protein-A with toxicity and mitogenicity in animal models and humans (see, for example, Bensinger et al., J. Biol. Resp. Modif. 3, 347, 1984; Messerschmidt et al., J. Biol. Resp. Modif. 3,325, 1984; Terman and Bertram, Eur. J. Cancer Clin. Oncol. 21, 1115; 1985; and Ventura et al., Hortobagyl. Cancer Treat Rep. 71, 411, 1987).

Furthermore, co-binding of Protein-A to human $V_H$-III domains is the main reason for causing elution pH differences in affinity chromatography amongst several IgG antibodies. Such differences are not desirable because it causes a lack of consistency in purification procedures among different monoclonal antibodies (Mabs). Furthermore, tightly bound IgG Mabs, due to co-binding of Protein-A to human VH-III, often require a lower pH value of the eluens in order to obtain efficient recoveries.

Protein-G is a bacterial surface protein expressed by group C and G streptococci. Like Protein-A, Protein-G also recognizes a common site at the interface between $C_H2$ and $C_H3$ domains on the Fc part of human IgG1, IgG2, IgG3 and IgG4 antibodies (Fey). Compared to Protein-A, a broader range of IgG species can be recognized. In addition, Protein-G shows binding to the Fab portion of IgG antibodies through binding to the $C_H1$ domain of IgG. Binding affinity towards $C_H1$ (±200 nM) is again significantly lower compared to its epitope on the Fc part. Although Protein-G has a wider reactivity profile than Protein-A, the binding of antibodies to Protein-G is often stronger, making elution and complete antibody recovery more difficult.

The most commonly used ligand for affinity purification of human immunoglobulins, in particular IgG's, for large-scale process applications is Protein-A. However, protein-A lacks the capability of binding to human antibodies of the IgG3 subclass. In addition, Protein-A and G strongly bind to the CH2-CH3 interface on the Fc portion of IgG antibodies. Experimental data indicate that induced fit occurs, which may explain the harsh conditions required for elution. These harsh conditions may affect the conformation of the binding sites, thereby altering the immune function of purified IgG antibodies (P. Gagnon, 1996, in Purification tools for monoclonal antibodies, published by Validated Biosystems, Inc 5800N). X-ray crystallographic measurements have shown that through binding to Protein-A, the CH2 domains can be displaced longitudinally towards the CH3 domains, which finally causes partial rotation and destabilization of the carbohydrate region between the CH2 domains. The distortion interferes with subsequent protein-protein interactions that are required for the IgG to exert its effector functions. Aside from the consequences of harsh elution conditions (especially for Protein-G) on the antigen binding capabilities, these secondary effects sometimes interfere with or alter antibody effector functions and increased susceptibility of immunoglobulins to proteolysis. Loss of effector functions, caused by denaturation, altered folding and chemical modifications that arise during purification steps, are highly undesirable if the human or humanized antibodies are to be used for therapeutic purposes. In particular, reduction of intra- and inter-molecular sulphur bridges is often a problem that arises during purification and storage.

As alternative to human IgG binding proteins like Protein-A and G, several mouse monoclonal antibodies (Mabs) have been described in literature that are capable of binding to the Fc domain of human IgG antibodies. (Nelson P N, et al. Characterisation of anti-IgG monoclonal antibody A57H by epitope mapping. Biochem Soc Trans 1997; 25:373.)

Some common Fc epitopes have been identified and a number of examples are listed below: Mabs G7C, JD312 have a binding epitope on CH2, amino acids 290-KPREE-294 (SEQ ID NO: 201). Mabs PNF69C, PNFI 10A, PNF211C, have a binding epitope on CH2-CH3, AA: 338-KAKGQPR-344 (SEQ ID NO: 202). Mab A57H shows binding epitope on CH3, AA 380-EWESNGQPE-388 (SEQ ID NO: 203). A problem associated with the use of mouse monoclonals, or monoclonals from other non-human species, is the release of Mabs from the matrix which causes contamination in the purified preparations that is difficult to remove. Furthermore, monoclonal antibodies and functional fragments thereof (Fab, Fab2) are easily denatured and S—S bridges, keeping the 3D structure of the molecule and the heavy and light chain aligned, are easily disrupted, in particular under harsh elution conditions that are oftentimes required for release of column bound human IgG's. Due to the vulnerability of the affinity ligands the capacity of the column is rapidly reduced, and columns have a very limited re-use capacity after elution and are unsuitable for continuous operation.

Instead of (sc)Fv fragments as described in EP-A-434317, antibody fragments derived from antibodies naturally devoid of light chains (VHH) as described in WO2006/059904 can also be used to generate immunosorbent materials for the purification of human IgG antibodies. Advantage of use of these VHH fragments are that they are single domain peptides, which are exceptionally stable even at higher temperatures. Furthermore, VHH's, are small and easily produced in cost-efficient host organisms such as *Saccharomyces cerevisiae*. In addition, due to the sequence similarity between these VHH fragments and the human $V_H$-III domain family, immunogenecity is expected to be very low compared to bacterial surface proteins like Protein-A and G. These antibodies are described in more detail in EP-A-656946.

However, the amino acid sequences as described in WO2006/059904 relate to VHH fragments that bind to the light chain of human antibodies of either the kappa or lambda isotype, and as such do not enable selective purification of antibodies of the IgG isotype only.

DESCRIPTION OF THE INVENTION

We have found a new class antigen-binding proteins that are useful for incorporation into and/or attachment to immunoadsorbent materials for the selective purification of mammalian IgG antibodies, including human IgG antibodies, through binding of an epitope that is present in the Fc domain of such IgG antibodies.

In a first aspect, the present invention relates to an antigen-binding protein that specifically binds to a mammalian IgG. Preferably, the antigen-binding protein comprising an amino acid sequence that comprises 4 framework regions, FR1 to FR4, and 3 complementarity determining regions, CDR1 to CDR3, that are operably linked in the order FR1-CDR1-FR2-CDR2-FR3-CDR3-FR4, wherein: a) the CDR1 has an amino acid sequence selected from the group consisting of SEQ ID No's: 1-49 or an amino acid sequence that differs from SEQ ID No's: 1-49 in one or two of the amino acid residues; b) the CDR2 has an amino acid sequence having at least 80, 85, 90, 95, 98% sequence identity with an amino acid sequence selected from the group consisting of SEQ ID No's: 50-98; and, c) CDR3 is an amino acid sequence having at least 80, 85, 90, 95, 98% sequence identity with an amino acid sequence selected from the group consisting of SEQ ID No's: 99-147; and, wherein each of the framework regions has at least 50, 55, 60, 65, 70, 75, 80, 85, 90, 95 or 100% amino acid identity with the framework amino acid sequence of any one of SEQ ID No's: 148-196.

In a preferred embodiment, the antigen binding proteins of the invention are antibodies, more preferably such antibodies or fragments thereof are derived from antibodies naturally devoid of light chains. Antibodies naturally devoid of light chains may be obtained e.g. by immunisation of camelids (e.g. llama's) or sharks (see further below). These antibodies comprise heavy chains only and are devoid of light chains. The advantage of use of such single domain heavy chain antibodies is that they are exceptionally stable even at higher temperatures, small and are easily produced in host organisms such as *Saccharomyces cerevisiae*. Thus, an antigen-binding protein of the invention preferably comprises an immunoglobulin-derived variable domain that comprises a complete antigen binding site for an epitope on a target molecule in a single polypeptide chain. Such antigen-binding proteins specifically include but are not limited to:

1) antibodies obtainable from camelids and sharks that consist of only heavy chains and that are naturally devoid of light chains;

2) variable domains of the antibodies defined in 1), usually referred to as VHH domains;

3) engineered forms of the antibodies defined in 1) or domains in 2) such as e.g. "camelidised" antibodies in which frame work sequences of a camelid (or shark) VHH domain are grafted with CDRs obtained from other sources;

4) engineered forms of immunoglobuline-like variable domains in which frame works sequences from a variety of immunoglobuline-like molecules are combined with CDRs specific for a given target molecule as e.g. described in WO 04/108749.

In a preferred antigen-binding protein of the invention, the single polypeptide chain of the variable domain that comprises the full antigen-binding capacity preferably has an amino acid sequence and structure that can be considered to be comprised of four framework regions or "FR's", which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively. These framework regions and complementary determining regions are preferably are operably linked in the order FR1-CDR1-FR2-CDR2-FR3-CDR3-FR4 (from amino terminus to carboxy terminus).

The total number of amino acid residues in the variable domain with full antigen-binding capacity can be in the region of 110-135, and preferably is in the region of 115-129. However, a variable domain with full antigen-binding capacity in accordance with the invention is not particularly limited as to its length and/or size, as the domain meets the further functional requirements outlined herein and/or is suitable for the purposes described herein. The amino acid residues of a variable domain with full antigen-binding capacity are numbered according to the general numbering for VH domains given by Kabat et al. ("Sequence of proteins of immunological interest", US Public Health Services, NIH Bethesda, Md., Publication No. 91), as applied to VHH domains from Camelids by Riechmann and Muyldermans (1999, J. Immunol. Methods 231 (1-2): 25-38, see for example Fig. 2 of said reference) and by Harmsen et al. (2000, Molecular Immunology 37: 579-590, see for example Fig. 1 of said reference).

According to this numbering, in a variable domain with full antigen-binding capacity: FR1 comprises the amino acid residues at positions 1-25; CDR1 comprises the amino acid residues at positions 26-35; FR2 comprises the amino acids at positions 36-49; CDR2 comprises the amino acid residues at positions 50-64; FR3 comprises the amino acid residues at positions 65-94; CDR3 comprises the amino acid residues at positions 95-102; and, finally, FR4 comprises the amino acid residues at positions 103-113.

In this respect, it should be noted that—as is well known in the art for VH domains and for VHH domains—the total number of amino acid residues in each of the CDR's may vary and may not correspond to the total number of amino acid residues indicated by the Kabat numbering. However, based on the conserved amino acids of the frame work region a skilled person will be able to align the respective frame work and complementarity determining regions in accordance with the Kabat definitions for those variable domains with full antigen-binding capacity that have a length other than 113 amino acids. Examples thereof are given in the definition of the complementarity determining regions in the amino acid sequences of IgG-Fc 1-49 herein. Alternative methods for numbering the amino acid residues of VH domains, which methods can also be applied in an analogous manner to VHH domains from Camelids and to variable domains with full antigen-binding capacity, are the method described by Chothia et al. (Nature 342, 877-883 (1989)), the so-called "AbM definition" and the so-called "contact definition", or the IMGT numbering system (Lefranc et al., 1999, Nucl. Acids Res. 27: 209-212).

In a preferred antigen-binding protein of the invention, the frame work amino acid sequence of a variable domain with full antigen-binding capacity preferably has at least 50, 55, 60, 65, 70, 75, 80, 85, 90, 95 or 100% amino acid identity with the frame work amino acid sequence of any one of SEQ ID No's: 148-196.

More preferably, the amino acid residues that are present at each position (according to the Kabat numbering) of the FR1, FR2, FR3 and FR4 of the single polypeptide chain of the variable domain that comprises the full antigen-binding capacity preferably are as indicated in Tables 1 to 4 for FR1, FR2, FR3 and FR4. Thereby preferably the frame work amino acid residues of a variable domain with full antigen-binding capacity are chosen from the non-limiting residues in Tables 1 to 4 that can be present at each position (according to the Kabat numbering) of the FR1, FR2, FR3 and FR4 of naturally occurring Camelid VHH domains (data was taken from patent WO 2006/040153 PCT/EP2005/011018). More preferably, however, the frame work amino acid residues of a variable domain with full antigen-binding capacity are chosen from the amino acid residues in Tables 1 to 4 that are present at each position (according to the Kabat numbering) of the FR1, FR2, FR3 and FR4 of the amino acid sequences of any one of SEQ ID No's: 148-196, of antigen-binding proteins that specifically bind a mammalian IgG. For each position, the amino acid residue that most frequently occurs at each position is indicated in bold in Tables 1 to 4.

Thus, in a preferred embodiment of the invention, on the basis of the amino acid residues present on the positions described in Tables 1 to 4, the amino acid sequence of a variable domain comprising the full antigen-binding capacity in an antigen-binding protein of the invention can have the structure:

FR1-CDR1-FR2-CDR2-FR3-CDR3-FR4 in which FR1 has an amino acid sequence chosen from the group consisting of:
a) [1] QVQLQESGGGLVQAGGSLRLSCAAS [25] (SEQ ID: 197);
b) an amino acid sequence that has at least 50, 55, 60, 65, 70, 75, 80, 85, 90, 95 or 100% sequence identity with the sequence in a); and/or,
c) the amino acid sequence of a) that has one or more amino acid substitutions as defined in Table 1;
in which FR2 is chosen from the group consisting of the amino acid sequence:
d) [36] WFRQAPGKEREFVA [49] (SEQ ID: 198);
e) an amino acid sequence that has at least 50, 55, 60, 65, 70, 75, 80, 85, 90, 95 or 100% sequence identity with the sequence in d); and/or
f) the amino acid sequence of d) that has one or more amino acid substitutions as defined in Table 2; in which FR3 is chosen from the group consisting of the amino acid sequence:
g) [65] GRFTISRDNAKNTVYLQMDSLKPEDTAVYSCAA [94] (SEQ ID: 199);
h) an amino acid sequence that has at least 50, 55, 60, 65, 70, 75, 80, 85, 90, 95 or 100% sequence identity with the sequence in g); and/or,
i) the amino acid sequence of g) that has one or more amino acid substitutions as defined in Table 3; and,
in which FR4 is chosen from the group consisting of the amino acid sequence:
j) [103] WGQGTQVTVSS [113] (SEQ ID: 200);
k) an amino acid sequence that has at least 50, 55, 60, 65, 70, 75, 80, 85, 90, 95 or 100% sequence identity with the sequence in j); and/or,
l) the amino acid sequence of j) that has one or more amino acid substitutions as defined in Table 4.

In an alternative preferred embodiment, the antigen-binding protein of the invention comprises a CDR1, CDR2 and CDR3 combination as given in one of the rows of Table 5, wherein the framework regions (FR1 to FR4) may be any of the framework regions (FR1 to FR4) as defined above. More preferably, the antigen-binding protein of the invention comprises a CDR1, CDR2 and CDR3 combination as given in one of the rows of Table 5, wherein the antigen-binding protein has an amino acid sequence with at least 90, 95, 98, 99 or 100% sequence identity to the sequence provided in the last cell of the corresponding row of Table 5.

The antigen-binding protein of the invention is a component that specifically binds to the target molecule with the desired binding affinity (as herein defined). The antigen-binding protein of the invention preferably is a mono-specific antigen-binding protein. A composition comprising a mono-specific antigen-binding protein, such as the immunoadsorbant materials of the present invention, is understood to mean a composition having a homogeneous population of the antigen-binding protein. It follows that the mono-specific antigen-binding protein is specific for a single epitope or ligand. It is however expressly included in the invention that the immunoadsorbant material may comprise more than one type of mono-specific antigen-binding protein, each consisting of a homogeneous population. Usually, however, in the context of the present invention, an immunoadsorbant material will not comprise more than 4, 6, 8, 10 or 20 different mono-specific antigen-binding proteins. The antigen-binding protein will usually be an antibody or fragment thereof, in which case the mono-specific antigen-binding protein will thus be a monoclonal antibody or a fragment thereof, which may be obtained from a cloned cell-line (e.g. hybridoma) or expressed from a cloned coding sequence. The term mono-specific antigen-binding protein as used herein thus excludes polyclonal antibodies and antisera.

An antigen-binding protein of the invention, that can bind to, that has affinity for and/or that has specificity for a specific target molecule (antigenic determinant, epitope, antigen or protein) may be said to be "against" or "directed against" said target molecule. The term "specificity" refers to the number of different types of antigens or antigenic determinants to which a particular antigen-binding protein molecule can bind. The specificity of an antigen-binding protein can be determined based on affinity and/or avidity. The affinity, represented by the equilibrium constant for the dissociation of an antigen with an antigen-binding protein ($K_D$), is a measure for the binding strength between an antigenic determinant and an antigen-binding site on the antigen-binding protein. Alternatively, the affinity can also be expressed as the affinity constant ($K_A$), which is $1/K_D$. Affinity can be determined in a manner known per se, depending on the specific combination of antigen binding protein and antigen of interest. Avidity is herein understood to refer to the strength of binding of a target molecule with multiple binding sites by a larger complex of binding agents, i.e. the strength of binding of multivalent binding. Avidity is related to both the affinity between an antigenic determinant and its antigen binding site on the antigen-binding molecule and the number of binding sites present on the antigen-binding molecule. Affinity, on the other hand refers to simple monovalent receptor ligand systems.

Typically, antigen-binding proteins of the invention will bind the target molecule with a dissociation constant ($K_D$) of about $10^{-5}$ to $10^{-12}$ M or less, and preferably $10^{-7}$ to $10^{-12}$ M or less and more preferably $10^{-8}$ to $10^{-12}$ M or less, and/or with a binding affinity of at least $10^{-7}$ M, preferably at least $10^{-8}$ M, more preferably at least $10^{-9}$ M, such as at least $10^{-10}$, $10^{-11}$, $10^{-12}$ M or more. Any $K_D$ value greater than $10^{-4}$ M (i.e. less than 100 μM) is generally considered to indicate non-specific binding. Preferably, a polypeptide of the invention will bind to the desired antigen with an affinity less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art. In a preferred embodiment the antigen-binding protein of the invention will bind to the desired antigen with an affinity as defined above yet this affinity is combined an efficient release of the antigen from the antigen-binding protein under mild elution conditions.

Mild elution conditions are herein understood to be conditions under which the activity and/or integrity (e.g. secondary/tertiary structure) are only slightly affected (e.g. less than 10% inactive or denatured), preferably there is no detectable reduction in activity and/or integrity of the antigen. Examples of such mild elution conditions include e.g. the acidic conditions as specified herein below, including e.g. 0.1 M glycine pH 3.0 or pH 4.0, 0.1 M arginine pH 4.0 or pH 5.0. Other examples of mild elution conditions at (near)-neutral pH include e.g. high ionic strength such as condition equivalent 2 M NaCl (in e.g. 20 mM Tris pH 8.0) or chaotropic agents such as ethylene glycol or propylene glycol (40-60%, preferably about 50% (v/v), in e.g. 20 mM Imidazol, 10 mM $CaCl_2$, 0.01% Tween 80, 250 mM NaCl at pH7.0). Examples of antigen-binding proteins of the invention that release the antigen under mild elution condition as indicated above include antigen-binding proteins that have a structure as herein defined above wherein: a) the CDR1 has an amino acid sequence selected from the group consisting of SEQ ID No's: 1-9 and 16, and amino acid sequences that differs from SEQ ID No's: 1-9, and 16 in no more than 4, 3, 2, or 1 amino acid residues; b) the CDR2 has an amino acid sequence selected from the group consisting of SEQ ID No's: 50-58 and 65, and an amino acid sequences that differs from SEQ ID No's: 50-58 in no more than 6, 5, 4, 3, 2, or 1 amino acid residues; and, c) the CDR3 has an amino acid sequence selected from the group consisting of SEQ ID No's: 99-107 and an amino acid sequences that differs from SEQ ID No's: 99-107 and 114, in no more than 6, 5, 4, 3, 2, or 1 amino acid residues. More preferably the antigen-binding protein has an amino acid sequence selected from the group consisting of SEQ ID No's 148-156 and 163.

An epitope is defined as the portion of the target molecule that is bound by the antigen-binding protein. In case the antigen-binding protein is an antibody, the epitope is the portion of a target molecule that triggers an immunological response upon immunisation of an individual vertebrate host with this molecule. Generally it is the site of the target molecule where binding to an antibody takes place. The epitope is preferably present naturally in the target molecule. Optionally the epitope(s) is/are a sequence that has been artificially included in the target molecule. Optionally a multitude of the same or different epitopes is included in the target molecule to facilitate its purification and detection.

A target molecule is herein defined as a molecule that is to be bound by a binding agent, preferably an antigen-binding protein of the invention. A target molecule may be a protein that requires purification, or a protein that is to be detected or identified. A preferred target molecule in the context of the present invention is a mammalian IgG. Preferably, the antigen-binding protein binds to the Fc (Fragment crystallizable) domain of a mammalian immunoglobulin. More preferably the antigen-binding protein binds to Fc (Fragment crystallizable) domain of a mammalian IgG and does not bind to a mammalian immunoglobulin of the classes IgD, IgA, IgM or IgE. It is herein understood that antigen-binding protein that binds to a first type of target molecule and not to a second type of target molecule has a difference in dissociation constants for the first and second types of target molecules, respectively of at least a factor 100, 1000, 10,000 or 100,000. Preferably, the antigen-binding protein does not bind to the Fab (Fragment antigen binding) domain of the mammalian immunoglobulin. Preferably, binding of the antigen-binding protein to the mammalian immunoglobulin and subsequent elution of the immunoglobulin does not affect effector functions of the mammalian immunoglobulin. Also preferred is that binding of the antigen-binding protein to the mammalian immunoglobulin and subsequent elution of the immunoglobulin does not reduce, inhibit or otherwise affect binding of the mammalian immunoglobulin molecule to its predetermined antigen.

An antigen-binding protein of the invention that binds to an Fc domain of a mammalian IgG molecule is an antigen-binding protein that preferably has one or more properties selected from the group consisting of: a) the antigen-binding protein binds the human IgG molecule with a binding affinity of at least $10^{-7}$ M, $10^{-8}$ M, or $10^{-9}$ M as analyzed by BiaCore using polyclonal human IgG; b) the antigen-binding protein is obtainable by expression in yeast at an expression level of at least 0.5, 0.8, 1.0 g/L of yeast culture; c) the antigen-binding protein has a dynamic binding capacity of at least 2, 5 or 10 mg human IgG per ml of carrier, when coupled to NHS activated carrier (preferably Sepharose 4B fast flow) at a density of 20 mg antigen-binding protein per ml NHS carrier and using a flow-rate of 150 cm/h; d) human IgG bound to the antigen-binding protein when coupled to reference NHS carrier as defined in c) is recovered from the antigen-binding protein with a yield of at least 90, 95, or 99% using 0.1 M glycine, pH 2.0; e) human IgG bound to the antigen-binding protein when coupled to reference NHS carrier as defined in c) is recovered from the antigen-binding protein with a yield of at least 70, 75, or 80% using 0.1 M glycine pH 3.0; f) the antigen-binding protein when coupled to NHS carrier as defined in c) retains a residual dynamic binding capacity of at least 70, 75 or 80% after 20 cleaning-in-place cycles, wherein in each cleaning-in-place cycle the antigen-binding protein coupled to reference NHS carrier is contacted for 15 minutes with 0.05 M NaOH and 0.5 M NaCl at a flow rate of 150 cm/h; and g) the antigen-binding protein can be immobilized onto carriers and/or carriers via standard coupling chemistries (e.g. NHS or CNBr activated carriers) and still retain the functionality of IgG binding (i.e. has a dynamic binding capacity as defined in c)) without the need of additional tags or linkers genetically incorporated at the N- and/or C-terminus of the antigen-binding protein. More preferably, the antigen-binding protein has at least 4, 5, 6, or all of said properties. For convenience, throughout this specification a reference to "reference NHS carrier" refers to the NHS activated carrier (preferably Sepharose 4B fast flow) at a density of 20 mg antigen-binding protein per ml NHS carrier as defined in c) above.

A preferred antigen-binding protein of the invention binds to the Fc domain of a human IgG molecule but does not bind to an IgG molecule of murine or bovine origin. A preferred antigen-binding protein binds to one or more of human IgG1, IgG2, IgG3 and IgG4 molecules, more preferably the antigen-binding protein binds to all four human IgG subclasses. An antigen-binding protein that binds to the Fc domain of a human IgG molecule but does not bind to an IgG molecule of murine or bovine origin preferably is an antigen-binding protein having a structure as herein defined above wherein: a) the CDR1 has an amino acid sequence selected from the group consisting of SEQ ID No's: 1-15, 17-25, 31-36, 38, 43 and 44 and amino acid sequences that differs from SEQ ID No's: 1-15, 17-25, 31-36, 38, 43 and 44 in no more than 4, 3, 2 or 1 amino acid residues; b) the CDR2 has an amino acid sequence selected from the group consisting of SEQ ID No's: 50-64, 66-74, 80-85, 87, 92 and 93 and an amino acid sequences that differs from SEQ ID No's: 50-64, 66-74, 80-85, 87, 92 and 93 in no more than 6, 5, 4, 3, 2, or 1 amino acid residues; and, c) the CDR3 has an amino acid sequence selected from the group consisting of SEQ ID No's: 99-113, 115-123, 129-134, 136, 141 and 142 and an amino acid sequences that differs from SEQ ID No's: 99-113, 115-123, 129-134, 136, 141 and 142 in no more than 6, 5, 4, 3, 2, or 1 amino acid residues. More preferably the antigen-binding protein has an amino acid sequence selected from the group consisting of SEQ ID No's 148-162, 164-172, 178-183, 185, 190 and 191.

A more preferred antigen-binding protein of the invention binds to the Fc domain of a human IgG molecule but does not bind to an IgG molecule of murine, bovine or caprine (goat) origin. The antigen-binding protein preferably binds to one or more of human IgG1, IgG2, IgG3 and IgG4 molecules, more preferably the antigen-binding protein binds to all four human IgG subclasses. An antigen-binding protein that binds to the Fc domain of a human IgG molecule but does not bind to an IgG molecule of murine, bovine or caprine origin preferably is an antigen-binding protein having a structure as herein defined above wherein: a) the CDR1 has an amino acid sequence selected from the group consisting of SEQ ID No's: 1-15, 17-25, 31-36, 38 and 44 and amino acid sequences that differs from SEQ ID No's: 1-15, 17-25, 31-36, 38 and 44 in no more than 4, 3, 2 or 1 amino acid residues; b) the CDR2 has an amino acid sequence selected from the group consisting of SEQ ID No's: 50-64, 66-74, 80-85, 87 and 93 and an amino acid sequences that differs from SEQ ID No's: 50-64, 66-74, 80-85, 87 and 93 in no more than 6, 5, 4, 3, 2, or 1 amino acid residues; and, c) the CDR3 has an amino acid sequence selected from the group consisting of SEQ ID No's: 99-113, 115-123, 129-134, 136 and 142 and an amino acid sequences that differs from SEQ ID No's: 99-113, 115-123, 129-134, 136 and 142 in no more than 6, 5, 4, 3, 2, or 1 amino acid residues. More preferably the antigen-binding protein has an amino acid sequence selected from the group consisting of SEQ ID No's 148-162, 164-172, 178-183, 185 and 191.

An even more preferred antigen-binding protein of the invention binds to the Fc domain of a human IgG molecule but does not bind to an IgG molecule that originates from murine, bovine, caprine, rat, syrian hamster, guinea pig, dog, cat or sheep. The antigen-binding protein preferably binds to one or more of human IgG1, IgG2, IgG3 and IgG4 molecules, more preferably the antigen-binding protein binds to all four human IgG subclasses. The antigen-binding protein further preferably has one or more properties selected from the group consisting of: a) the antigen-binding protein binds the human IgG molecule with a binding affinity of at least 5 nM as analyzed by BiaCore using polyclonal human IgG; b) human IgG bound to the antigen-binding protein when coupled to reference NHS carrier is recovered from the antigen-binding protein with a yield of at least 99% using 0.1 M glycine, pH 2.0; and, c) human IgG bound to the antigen-binding protein when coupled to reference NHS carrier is recovered from the antigen-binding protein with a yield of at least 80% using 0.1 M glycine pH 3.0. More preferably the antigen-binding protein preferably has at least 2 or 3 of said properties. Such an antigen-binding protein further preferably has a structure as herein defined above wherein: a) the CDR1 has an amino acid sequence selected from the group consisting of SEQ ID No's: 1-15 and amino acid sequences that differs from SEQ ID No's: 1-15 in no more than 4, 3, 2 or 1 amino acid residues; b) the CDR2 has an amino acid sequence selected from the group consisting of SEQ ID No's: 50-64 and an amino acid sequences that differs from SEQ ID No's: 50-64 in no more than 6, 5, 4, 3, 2, or 1 amino acid residues; and, c) the CDR3 has an amino acid sequence selected from the group consisting of SEQ ID No's: 99-113 and an amino acid sequences that differs from SEQ ID No's: 99-113 in no more than 6, 5, 4, 3, 2, or 1 amino acid residues. More preferably the antigen-binding protein has an amino acid sequence selected from the group consisting of SEQ ID No's 148-162.

An most preferred antigen-binding protein of the invention binds to the Fc domain of a human IgG molecule but does not bind to an IgG molecule that originates from murine, bovine, caprine, rat, syrian hamster, guinea pig, dog, cat or sheep. The antigen-binding protein preferably binds to one or more of human IgG1, IgG2, IgG3 and IgG4 molecules, more preferably the antigen-binding protein binds to all four human IgG subclasses. The antigen-binding protein further preferably has one or more properties selected from the group consisting of: a) the antigen-binding protein binds the human IgG molecule with a binding affinity of at least 5 nM as analyzed by BiaCore using polyclonal human IgG; b) human IgG bound to the antigen-binding protein when coupled to reference NHS carrier is recovered from the antigen-binding protein with a yield of at least 99% using 0.1 M glycine, pH 3.0; c) human IgG bound to the antigen-binding protein when coupled to reference NHS carrier is recovered from the antigen-binding protein with a yield of at least 95% using 0.1 M glycine, pH 4.0; d) human IgG bound to the antigen-binding protein when coupled to reference NHS carrier is recovered from the antigen-binding protein with a yield of at least 99% using 0.1-0.2 M arginine, pH 3.0; e) retains a residual dynamic binding capacity of at least 90, 95 or 100% after 100 cleaning-in-place cycles, wherein in each cleaning-in-place cycle the antigen-binding protein coupled to reference NHS carrier is contacted for 15 minutes with 0.1 M NaOH at a flow rate of 150 cm/h; and f) retains a residual dynamic binding capacity of at least 80% after 40 cleaning-in-place cycles, wherein in each cleaning-in-place cycle the antigen-binding protein coupled to reference NHS carrier is contacted for 15 minutes with 0.2 M NaOH at a flow rate of 150 cm/h. More preferably the antigen-binding protein preferably has at least 2, 3, 4, 5 or 6 of said properties. Such an antigen-binding protein further preferably has a structure as herein defined above wherein: a) the CDR1 has an amino acid sequence selected from the group consisting of SEQ ID No's: 1-9 and amino acid sequences that differs from SEQ ID No's: 1-9 in no more than 4, 3, 2, or 1 amino acid residues; b) the CDR2 has an amino acid sequence selected from the group consisting of SEQ ID No's: 50-58 and an amino acid sequences that differs from SEQ ID No's: 50-58 in no more than 6, 5, 4, 3, 2, or 1 amino acid residues; and, c) the CDR3 has an amino acid sequence selected from the group consisting of SEQ ID No's: 99-107 and an amino acid sequences that differs from SEQ ID No's: 99-107 in no more than 6, 5, 4, 3, 2, or 1 amino acid residues. More preferably the antigen-binding protein has an amino acid sequence selected from the group consisting of SEQ ID No's 148-156.

An alternatively more preferred antigen-binding protein of the invention binds to the Fc domain of a human IgG molecule but does not bind to an IgG molecule that originates from murine, bovine, caprine, rat, syrian hamster, guinea pig, dog, cat or sheep. The antigen-binding protein preferably binds to one or more of human IgG1, IgG2, IgG3 and IgG4 molecules, more preferably the antigen-binding protein binds to all four human IgG subclasses. The antigen-binding protein further preferably has one or more properties selected from the group consisting of: a) the antigen-binding protein binds the human IgG molecule with a binding affinity of at least 3 nM as analyzed by BiaCore using polyclonal human IgG; and b) the antigen-binding protein is obtainable by expression in yeast at an expression level of at least 1.2 g/L of yeast culture. More preferably the antigen-binding protein preferably has both of said properties. Such an antigen-binding protein further preferably has a structure as herein defined above wherein: a) the CDR1 has an amino acid sequence selected from the group consisting of SEQ ID No's: 10-15 and amino acid sequences that differs from SEQ ID No's: 10-15 in no more than 4, 3, 2, or 1 amino acid residues; b) the CDR2 has an amino acid sequence selected from the group consisting of SEQ ID No's: 59-64 and an amino acid sequences that differs from SEQ ID No's: 59-64 in no more than 6, 5, 4, 3, 2, or 1 amino acid residues; and, c) the CDR3 has an amino acid sequence selected from the group consisting of SEQ ID No's: 108-113 and an amino acid sequences that differs from SEQ ID No's: 108-113 in no more than 6, 5, 4, 3, 2, or 1 amino acid residues. More preferably the antigen-binding protein has an amino acid sequence selected from the group consisting of SEQ ID No's 157-162.

A preferred alternative antigen-binding protein of the invention binds to the Fc domain of an IgG molecule from at least two different species selected from the group consisting of human, murine, and bovine. Such a preferred alternative antigen-binding protein preferably has a structure as herein defined above wherein: a) the CDR1 has an amino acid sequence selected from the group consisting of SEQ ID No's: 16, 26-30, 37, 42 and 47-49 and amino acid sequences that differs from SEQ ID No's: 16, 26-30, 37, 42 and 47-49 in no more than 4, 3, 2 or 1 amino acid residues; b) the CDR2 has an amino acid sequence selected from the group consisting of SEQ ID No's: 65, 75-79, 86, 91 and 96-98 and an amino acid sequences that differs from SEQ ID No's: 65, 75-79, 86, 91 and 96-98 in no more than 6, 5, 4, 3, 2, or 1 amino acid residues; and, c) the CDR3 has an amino acid sequence selected from the group consisting of SEQ ID No's: 114, 124-128, 135, 140 and 145-147 and an amino acid sequences that differs from SEQ ID No's: 114, 124-128, 135, 140 and 145-147 in no more than 6, 5, 4, 3, 2, or 1 amino acid residues. More preferably the antigen-binding protein has an amino acid sequence selected from the group consisting of SEQ ID No's 163, 173-177, 184, 189 and 194-196.

A more preferred alternative antigen-binding protein of the invention binds to the Fc domain of an IgG molecule from a human, murine, bovine, rat, rabbit, dog, cat, swine, sheep, primate (of which at least chimpanzee and rhesus), donkey, and horse. Such a preferred alternative antigen-binding protein preferably has a structure as herein defined above wherein: a) the CDR1 has an amino acid sequence selected from the group consisting of SEQ ID No's: 16, 28-30, 37, 42 and 47-49 and amino acid sequences that differs from SEQ ID No's: 16, 28-30, 37, 42 and 47-49 in no more than 4, 3, 2 or 1 amino acid residues; b) the CDR2 has an amino acid sequence selected from the group consisting of SEQ ID No's: 65, 77-79, 86, 91 and 96-98 and an amino acid sequences that differs from SEQ ID No's: 65, 77-79, 86, 91 and 96-98 in no more than 6, 5, 4, 3, 2, or 1 amino acid residues; and, c) the CDR3 has an amino acid sequence selected from the group consisting of SEQ ID No's: 114, 126-128, 135, 140 and 145-147 and an amino acid sequences that differs from SEQ ID No's: 114, 126-128, 135, 140 and 145-147 in no more than 6, 5, 4, 3, 2, or 1 amino acid residues. More preferably the antigen-binding protein has an amino acid sequence selected from the group consisting of SEQ ID No's 163, 175-177, 184, 189 and 194-196.

The most preferred alternative antigen-binding protein of the invention is a "multi-species antigen-binding protein" that binds to the Fc domain of an IgG molecule from human, bovine, mouse, rat, rabbit, dog, cat, swine, sheep, primate (chimpanzee, rhesus), donkey, horse, goat, syrian hamster, guinea pig. More preferably this antigen-binding protein binds to the Fc domain of an IgG molecule from at least some, or preferably all species within the orders carnivores, even- and odd-toed ungulates, primates, rodents and Lagomorpha (including rabbits), most preferably this antigen-binding protein binds to the Fc domain of an IgG molecule from all mammalian species. The antigen-binding protein further preferably has one or more properties selected from the group consisting of: a) the antigen-binding protein binds the human IgG molecule with a binding affinity of at least 20 nM as analyzed by BiaCore using polyclonal human IgG; b) the antigen-binding protein is obtainable by expression in yeast at an expression level of at least 2.5 g/L of yeast culture; and c) human IgG bound to the antigen-binding protein when coupled to reference NHS carrier is recovered from the antigen-binding protein with a yield of at least 99% using 0.1 M glycine, pH 3.0 or 0.2 M arginine, pH 3.0. More preferably the antigen-binding protein preferably has at least 2 or 3 of said properties. The most preferred alternative antigen-binding protein preferably has a structure as herein defined above wherein a) the CDR1 has an amino acid sequence selected from the group consisting of SEQ ID No's: 16, 28-30 and 48 or an amino acid sequences that differs from SEQ ID No's: 16, 28-30 and 48 in no more than 4, 3, 2, or 1 amino acid residues; b) the CDR2 has an amino acid sequence selected from the group consisting of SEQ ID No's: 65, 77-79 and 97 or an amino acid sequences that differs from SEQ ID No's: 65, 77-79 and 97 in no more than 6, 5, 4, 3, 2, or 1 amino acid residues; and, c) the CDR3 has an amino acid sequence selected from the group consisting of SEQ ID No's: 114, 126-128 and 146 or an amino acid sequences that differs from SEQ ID No's: 114, 126-128 and 146 in no more than 6, 5, 4, 3, 2, or 1 amino acid residues. More preferably the antigen-binding protein has an amino acid sequence selected from the group consisting of SEQ ID No: 163, 175-177 and 195.

In one embodiment the invention pertains to particular form of an antigen-binding protein of the invention: a multivalent antigen-binding protein. The multivalent antigen-binding protein comprises the amino acid sequences of at least two antigen-binding proteins as defined herein above. The amino acid sequences of at least two antigen-binding proteins may be different from each or they may be identical, e.g. copies or repeats of one amino acid sequence. The amino acid sequences of the at least two antigen-binding proteins will usually be fused head-to tail, i.e. the C-terminus of the most N-terminal sequence fused to the N-terminus of the second sequence and so on. The amino acid sequences of at least two antigen-binding proteins may be fused directly linked or via a linker or spacer. Multivalent antigen-binding proteins of the invention may be produced by expression of a nucleotide sequence encoding the multivalent protein wherein two or more coding sequences of the antigen-binding proteins are operably linked together in the same reading frame. The skilled person will know how to operably fuse protein coding sequences.

In a further aspect the invention relates to a fusion protein wherein the amino acid sequence of an antigen-binding proteins as defined herein is fused with an amino acid sequence of a therapeutic protein. The two amino acid sequences are preferably linked together by a genetic fusion wherein nucleotide sequences encoding the respective amino acid sequences are operably linked together in frame by means known per se in the art. The amino acid sequences may be linked directly or optionally through a spacer or linker amino acid sequence. The fusion proteins comprising an amino acid sequence of an antigen-binding protein of the invention fused to a therapeutic protein are useful in increasing the serum half-life of the proteins. Injected biotherapeutics may be rapidly cleared from the blood circulation after administration, requiring high doses or frequent administration to maintain effective therapeutic levels. To overcome these problems, the biotherapeutic proteins or peptides can be bound to circulating serum proteins such as IgGs to enhance their bioavailability. In the present invention the biotherapeutic proteins or peptides are bound to circulating IgGs by fusing the amino acid sequence of the biotherapeutic protein or peptide to that of an antigen-binding protein of the invention. This will enhance the bioavailability of the fused biotherapeutic protein or peptide. The genetic fusion of the antigen-binding proteins of the invention to biotherapeutics can provide a binding moiety directed to the Fc domain of IgG, resulting in increased half-life of the biotherapeutic in serum. Harmsen et al., (2005, Vaccine 23 (41), p. 4926-42) have indeed reported that binding of a model VHH with therapeutic potential to porcine IgG through a fusion with a VHH that binds porcine IgG resulted in an increase in the in vivo residence of the model VHH compared to a control fusion VHH that did not bind to porcine IgG. This method of improving serum half-life may be applied in principle to any biotherapeutic protein, including e.g. antigens (for vaccination), enzymes (for enzyme replacement therapy), hormones, chymokines, interleukins, (humanised) monoclonal antibodies, and the like.

In another aspect the invention relates to a nucleic acid comprising a nucleotide sequence encoding an antigen-binding protein as defined herein above. A preferred nucleic acid according to the invention is a nucleic acid construct, wherein the nucleotide sequence encoding the antigen-binding protein is operably linked to a promoter and optionally other regulatory elements such as e.g. terminators, enhancers, polyadenylation signals, signal sequences for secretion and the like. Such nucleic acid constructs are particularly useful for the production of the antigen-binding proteins of the invention using recombinant techniques in which a nucleotide sequence encoding the antigen-binding protein of interest is expressed in suitable host cells such as described in Ausubel et al., "Current Protocols in Molecular Biology", Greene Publishing and Wiley-Interscience, New York (1987) and in Sambrook and Russell (2001) "Molecular Cloning: A Laboratory Manual ($3^{rd}$ edition), Cold Spring Harbor Laboratory, Cold Spring Harbor Laboratory Press, New York). As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

In a further aspect the invention pertains to a host cell comprising a nucleic acid as defined above. Preferably the host cell is a host cell for production of antigen-binding protein of the invention. The host cell may be any host cell capable of producing an antigen-binding protein of the invention, including e.g. a prokaryotic host cell, such as e.g., *E. coli*, or a (cultured) mammalian, plant, insect, fungal or yeast host cell, including e.g. CHO-cells, BHK-cells, human cell lines (including HeLa, COS and PER.C6), Sf9 cells and Sf+ cells. A preferred host cell for production of an antigen-binding protein of the invention is however a cell of an eukaryotic microorganism such as yeasts and filamentous fungi. Preferred yeast host cell e.g. include e.g. *Saccharomyces cerevisiae, Pichia pastoris, Hansenula polymorpha*, and *Kluyveromyces lactis*. Preferred strains, constructs and fermentation conditions for production of the antigen-binding protein of the invention are described by van de Laar, et al., (2007, Biotechnology and Bioengineering, Vol. 96, No. 3: 483-494). For example, production of the antigen-binding proteins can be performed in standard bioreactors with a working volume between 10 and 10,000 liters. Dissolved oxygen can be controlled by automatic adjustment of the impeller speed. The pH can be controlled using phosphoric acid and ammoniac gas or ammonia solution and temperature controlled via e.g. a cooling jacket and heating jacket. The offgas is analysed on ethanol concentration, $rO_2$ and $rCO_2$. The batch phase is started by adding 3%-8% of full-grown inoculum (e.g. 30° C., 0.3-0.4 VVM air, $DO_2$ minimum 30%, pH 5.0). When the ethanol concentration in offgas is declining in batch phase the ethanol fermentation can be started. The feed can be applied according to a pulsed feed profile to maintain the ethanol level within the demanded margins. The feed phases can be performed at 21° C. and 0.7-1.1 VVM air. During the ethanol fermentations $DO_2$ decreases to 0% and accumulated ethanol can be further controlled by a pulsed feed profile. Feed phase stops when the ethanol feed is depleted. The broth can be chilled to a temperature between 5-10° C. till further processing like biomass removal etc. (VVM=volumes of air per minute per volume of batch). In this context it is also understood that whenever herein we an antigen-binding protein of the invention as being obtainable by expression in yeast at a certain minimal expression level, this level is obtained using the method as described in Example 1.1. herein, whereby the (maximal) concentration of the antigen-binding protein (at the end of fermentation) "g/L" refers to the amount of secreted antigen-binding protein (in grams) per liter of cell-free broth (i.e., after removal of biomass by e.g. filtration).

Examples of antigen-binding proteins of the invention that are obtainable by expression in yeast at an expression level of at least 1.2 g/L of yeast culture include antigen-binding proteins that have a structure as herein defined above wherein: a) the CDR1 has an amino acid sequence selected from the group consisting of SEQ ID No's: 10-16 and amino acid sequences that differs from SEQ ID No's: 10-16 in no more than 4, 3, 2, or 1 amino acid residues; b) the CDR2 has an amino acid sequence selected from the group consisting of SEQ ID No's: 59-65 and an amino acid sequences that differs from SEQ ID No's: 59-65 in no more than 6, 5, 4, 3, 2, or 1 amino acid residues; and, c) the CDR3 has an amino acid sequence selected from the group consisting of SEQ ID No's: 108-114 and an amino acid sequences that differs from SEQ ID No's: 108-114 in no more than 6, 5, 4, 3, 2, or 1 amino acid residues. More preferably the antigen-binding protein has an amino acid sequence selected from the group consisting of SEQ ID No's 157-163.

Thus, in yet another aspect the invention relates to a method for producing an antigen-binding protein of the invention, wherein the method preferably comprises the steps of: a) culturing a host cell as defined above under conditions conducive to expression of the antigen-binding protein; and optionally, b) purifying the antigen-binding protein from at least one of the host cell and the culture medium. Suitable conditions may include the use of a suitable medium, the presence of a suitable source of food and/or suitable nutrients, a suitable temperature, and optionally the presence of a suitable inducing factor or compound (e.g. when the nucleotide sequences of the invention are under the control of an inducible promoter); all of which may be selected by the skilled person. Under such conditions, the amino acid sequences of the invention may be expressed in a constitutive manner, in a transient manner, or only when suitably induced. The antigen-binding proteins of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g. using a specific, cleavable amino acid sequence fused with the amino acid sequence of the invention) and/or preparative immunological techniques (i.e. using antibodies against the antigen-binding protein to be isolated).

In one aspect the invention also relates to a composition comprising an antigen-binding protein as defined herein. A preferred embodiment thereof is an immunoadsorbent material comprising the antigen-binding protein. An immunoadsorbent material is herein understood to mean the combination of a carrier and an antigen-binding protein that is immobilized on the carrier. Preferably in the immunoadsorbent material the antigen-binding protein is immobilized onto a carrier, whereby more preferably, the antigen-binding protein is immobilised onto the carrier by a covalent link. The carrier may be any material that may be used to for immobilization of an antigen-binding protein. Suitable examples are matrix materials, to entrap the binding agent, cell surfaces on which the binding agent is displayed and polymers that can be covalently linked to the binding agent. The person skilled in the art of affinity chromatography is well aware of suitable carriers such as e.g. porous solid phase carrier materials such as agarose, polystyrene, controlled pore glass, cellulose, dextrans, kieselguhr, synthetic polymers such as Sepharose™, porous amorphous silica. The carrier materials may be in any suitable format such as particles, powders, sheets, beads, filters and the like. Further specifications of suitable carrier materials are for example disclosed in EP-A-434317. Methods are available for immobilizing ligands quickly, easily and safely through a chosen functional group. The correct choice of coupling method depends on the substance to immobilized. For example the following commercially known derivatives of Sepharose™ allow the convenient immobilization of proteins thereon: CNBr-activated Sepharose™ 4B enables ligands containing primary amino groups to be rapidly immobilized by a spontaneous reaction. AH-Sepharose™ 4B and CH-Sepharose™ 4B both have a six-carbon long spacer arm and permit coupling via carboxyl and amino groups respectively. Flexible spacers are suitable for use in situations where the flexibility of the target molecules is limited or where 3-dimensional structure of the target requires some flexibility of the binding agent to allow optimal binding. Activated CH-Sepharose™ 4B provides a six-carbon spacer arm and an active ester for spontaneous coupling via amino groups. These are only a few examples of suitable immobilisation routes. Optionally the immunoadsorbent material is put into a column to facilitate easy chromatographic separations.

In yet a further aspect the invention relates to a method for the purification of a mammalian IgG molecule. The method preferably comprises the steps of: a) bringing a composition comprising a target molecule, e.g. a mammalian IgG molecule, in contact with the immunoadsorbent material comprising an antigen-binding protein of the invention, preferably under conditions that allow binding of the target molecule to the immunoadsorbent material; b) optionally, performing one or more washing steps; c) eluting the bound target molecule under conditions that decrease the affinity between the target molecule and the immunoadsorbent material; and, d) optionally, further processing target molecule.

The composition comprising the target molecule will often be an aqueous composition comprising many other proteins besides the target that is to be purified. The conditions of the contact step are preferably such that binding of the binding agent, to the target molecule occurs. Preferably in this step a loading buffer having pH around 6.5 to 8 is used. A suitable buffer is e.g. a PBS buffer or similar buffer a physiological ionic strength and pH. It is preferred that the loaded material washed until the non specific binders have eluted. This is usually done by rinsing with a suitable buffer, which may be the same as the loading buffer. Desorption or elution of the target molecule is the next step. This is preferably done by changing the conditions such that the antibody or fragment no longer binds the target molecule. Elution may be achieved by changing the conditions with respect to pH, salt, temperature or any other suitable measure. A preferred elution method for desorption is elution with a buffer having a pH below 4, 3 or 2. Suitable elution buffers are described herein above.

More specifically the invention relates to a method for the purification of a target molecule by immunoaffinity comprising the steps of: a) selecting an antigen-binding protein or fragment thereof, that binds to the target molecule; b) binding the antigen-binding protein or fragment thereof to immunonoadsorbent material; c) loading the immunoadsorbent material with a composition comprising the target molecule, preferably under conditions where binding of the antigen-binding protein to the target molecule takes place; d) washing the loaded immunoadsorbent to remove non specific binders; and, e) eluting the target molecule by applying elution conditions. Preferably a fragment of the antigen-binding protein retains binding affinity as defined above in the context of this invention.

In again a further aspect, the invention pertain to the use of an antigen-binding protein as defined herein for the detection and/or purification of a mammalian IgG molecule.

In one aspect the invention relates to methods for therapeutic apheresis. Therapeutic apheresis is an extracorporeal blood treatment to eliminate pathogenic compounds from the blood (Bosch, 2003, J. Artif. Organs 6(1): 1-8). One example of TA concerns the adsorption of antibodies in a variety of antibody-mediated immune diseases. A commonly used matrix for adsorption of antibodies in TA is Protein A sepharose. This matrix is used for the treatment of various auto-immune diseases and antibody-mediated transplant rejections. However, due to low affinity for human IgG subclass 3 antibodies, Protein A matrix is not efficient in the removal of IgG3 antibodies. Advantageously, the antigen-binding proteins of the present invention that are specific for mammalian or human IgG can also be used for the depletion of IgG, including IgG3, in patients suffering from antibody-mediated diseases. Preferably the method for therapeutic apheresis comprises at least one of removing, depleting and inactivating mammalian IgG in (from) a body fluid. Preferably the removing, depleting and inactivating of mammalian IgG in (from) a body fluid is performed ex vivo. The body fluid preferably is blood, a blood fraction such as e.g. blood plasma or blood serum, or another body fluid. In the method an antigen-binding protein of the invention as defined hereinabove or an immunoadsorbent material comprising the antigen-binding protein as defined above, is brought into extracorporeal contact with the body fluid of a subject, preferably a human subject. The immunoadsorbent apheresis material may be in the form of particles or beads, which may advantageously be packed into a flow chamber or a column, through which the body fluid of the subject or patient is passed extracorporeally. Before or after a treatment in which IgG is depleted, one or more further treatment stages for the body fluid can be carried out. Several treatments of the body fluid can be carried out in successive units, in which IgG is depleted by adsorption, to achieve the desired end concentration of IgG. Samples of the body fluid before and after IgG depletion may be tested using e.g. ELISA for IgG levels (using e.g. the antigen-binding proteins of the invention). The body fluid may then be reinfused into the subject or human patient, although the latter step may be explicitly excluded from a preferred extracorporal embodiment of the method. In preferred embodiments the methods of the invention for therapeutic apheresis are applied on body fluids from patient or subjects suffering from an antibody-mediated autoimmune disease, antibody-mediated transplant rejection or an autoimmune disease with an antibody-mediated component. Examples of such diseases include Myasthenia gravis, Goodpasture syndrome, Systemic Lupus Erythematosis (SLE) and dilated cardiomyopathy (DCM). The apheretic methods of the invention are particularly useful for autoimmune diseases in which auto-antibodies of subclass 3 are involved, like e.g. SLE and DCM, as IgG3 is not efficiently depleted using Protein A (Staudt et al., 2002, Circulation 106: 2448-2453).

In one aspect the invention thus pertains to the use of an antigen-binding protein of the invention that binds a mammalian IgG molecule for extracorporeal removal or depletion of mammalian IgG in a subject's body fluid, preferably a human subject.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

TABLE 1

Non-limiting examples of amino acid residues in FR1

| | Position | | | | | | | | | | | | | | | | | | | | | | | | |
|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
| a.a.residue | Q | V | Q | L | Q | E | S | G | G | G | L | V | Q | A | G | G | S | L | R | L | S | C | A | A | S |
| anti-IgG Fc | | | | | | D | | | | | | | | P | | D | | V | K | V | A | | V | P | L |
| a.a. sequences | | | | | | | | | | | | | | T | | E | | | | | | | R | V | |
| | | | | | | | | | | | | | | | | | | | | | | | S | D | |
| a.a.residue | A | | K | | E | Q | F | | | D | M | A | E | Q | | A | F | | L | F | F | | D | I | A |
| Camelid VHH's | E | | | | L | A | | | | R | S | | K | A | | | | | N | I | T | | E | L | F |
| | | | | | V | | | | | | V | | P | G | | | | | S | | | | P | S | P |
| | | | | | | | | | | | W | | R | S | | | | | T | | | | T | T | T |
| | | | | | | | | | | | | | | V | | | | | | | | | | | |

TABLE 2

Non-limiting examples of amino acid residues in FR2

| | Position | | | | | | | | | | | | | |
|---|---|---|---|---|---|---|---|---|---|---|---|---|---|---|
| | 36 | 37 | 38 | 39 | 40 | 41 | 42 | 43 | 44 | 45 | 46 | 47 | 48 | 49 |
| a.a.residue<br>anti-IgG Fc a.a. sequences | W | F<br>Y<br>H<br>I<br>V | R | Q<br>R<br>E | A<br>L<br>T<br>P<br>V<br>G | P<br>L | G | K<br>N<br>T<br>A | E<br>Q<br>G | R<br>L | E | F<br>L<br>S<br>A<br>G<br>W | V<br>L | A<br>S<br>G |
| a.a.residue<br>Camelid VHH's | | L | | H<br>P | F | A<br>S | E | D<br>E<br>Q<br>R<br>V | A<br>D<br>R<br>S<br>L | C<br>I<br>L<br>P<br>Q<br>V | D<br>K<br>Q<br>V | I<br>M<br>R<br>V<br>Y | I | T<br>V |

TABLE #3

Non-limiting examples of amino acid residues in FR3

| | Position | | | | | | | | | | | | | | | | | |
|---|---|---|---|---|---|---|---|---|---|---|---|---|---|---|---|---|---|---|
| | 65 | 66 | 67 | 68 | 69 | 70 | 71 | 72 | 73 | 74 | 75 | 76 | 77 | 78 | 79 | 80 | 81 | 82 |
| a.a.residue<br>anti-IgG Fc<br>a.a. sequences | G<br>A<br>D | R | F | T<br>A | I<br>V<br>T | S<br>F<br>Y | R<br>G<br>K<br>N<br>M<br>S | D<br>E | N<br>R<br>S<br>K<br>Y<br>G | A<br>T<br>V<br>P<br>G | K<br>Q<br>G<br>N<br>H<br>E | N<br>D<br>Y<br>T<br>K | T<br>M<br>A | V<br>M<br>I<br>A<br>G<br>E<br>L | Y<br>F<br>H<br>D<br>S<br>N<br>F | L | Q<br>E<br>V<br>L | M<br>L<br>I<br>V |
| a.a.residue<br>Camelid VHH's | | | L<br>V | N<br>S | L<br>M | A<br>T | H<br>I<br>L<br>Q<br>T<br>W | G<br>N<br>V | A<br>D<br>F<br>I<br>L<br>T<br>V | D<br>N<br>S | A<br>L<br>R | R<br>S | E<br>I<br>P<br>S | F | A | F<br>V | I<br>R<br>T | |

| | Position | | | | | | | | | | | | | | |
|---|---|---|---|---|---|---|---|---|---|---|---|---|---|---|---|
| | 82a | 82b | 82c | 83 | 84 | 85 | 86 | 87 | 88 | 89 | 90 | 91 | 92 | 93 | 94 |
| a.a.residue<br>anti-IgG Fc<br>a.a. sequences | N<br>S<br>T<br>D | S<br>N | L<br>I | K<br>Q<br>E<br>R | P<br>A<br>L<br>V<br>F | E<br>D | D | T | A<br>G | V<br>M<br>I<br>S<br>R | Y | Y<br>F<br>L<br>S | C | A<br>N<br>H<br>V<br>Y<br>S<br>F | A<br>I<br>G<br>R<br>T |
| a.a.residue<br>Camelid VHH's | G<br>H | D<br>G<br>R<br>T | P<br>V | N<br>G<br>I<br>M<br>T | D<br>R<br>S<br>T | G<br>Q | | A<br>S | S | A<br>D<br>L<br>M<br>N<br>T | F | D<br>H<br>T<br>V | | G<br>K<br>R<br>T | V<br>C<br>F<br>K<br>L<br>S |

TABLE 4

Non-limiting examples of amino acid residues in FR4

| | Position | | | | | | | | | | |
|---|---|---|---|---|---|---|---|---|---|---|---|
| | 103 | 104 | 105 | 106 | 107 | 108 | 109 | 110 | 111 | 112 | 113 |
| a.a.residue<br>anti-IgG Fc a.a. sequences | W | G<br>R<br>A | Q<br>K<br>P | G | T | Q<br>L | V<br>I | T<br>A<br>N | V | S | S |
| a.a.residue<br>Camelid VHH's | P<br>R<br>S | D | E<br>R | | A<br>I | R | | I | A<br>I | F | A<br>L<br>P<br>T |

DESCRIPTION OF THE FIGURES

FIG. 1. In FIG. 1 the residual dynamic binding capacities (DBCs) after cycles with 0.1 M NaOH (open diamonds) and 0.2 M NaOH (open squares) are presented.

EXAMPLES

Example 1

Identification of IgG-Fc Domain Binding VHH Fragments

The IgG-Fc domain binding VHH fragments were identified from llamas immunized with mammalian IgG antibodies and/or Fc fragments thereof. Screening of individual VHH fragments was performed by ELISA using IgG from different mammalian species and/or Fc—and Fab fragments thereof, including non-IgG antibodies like IgM and IgA, which resulted in a panel of VHH fragments binding to the Fc domain of mammalian IgG and human IgG in particular. Table 5 presents the CDR1, CDR2 and CDR3 amino acid sequences that are comprised in each of the VHH fragments and also the amino acid sequence of each of the VHH fragments including the framework regions.

TABLE 5

CDR1, CDR2 and CDR3 amino acid sequences in each of the clones and the amino acid sequence of each clone including the framework regions (FR)

| VHH | CDR1 | CDR2 | CDR3 | VHH fragment including FR |
|---|---|---|---|---|
| IgG-Fc-01 | SEQ ID NO: 1 | SEQ ID NO: 50 | SEQ ID NO: 99 | SEQ ID NO: 148 |
| IgG-Fc-02 | SEQ ID NO: 2 | SEQ ID NO: 51 | SEQ ID NO: 100 | SEQ ID NO: 149 |
| IgG-Fc-03 | SEQ ID NO: 3 | SEQ ID NO: 52 | SEQ ID NO: 101 | SEQ ID NO: 150 |
| IgG-Fc-04 | SEQ ID NO: 4 | SEQ ID NO: 53 | SEQ ID NO: 102 | SEQ ID NO: 151 |
| IgG-Fc-05 | SEQ ID NO: 5 | SEQ ID NO: 54 | SEQ ID NO: 103 | SEQ ID NO: 152 |
| IgG-Fc-06 | SEQ ID NO: 6 | SEQ ID NO: 55 | SEQ ID NO: 104 | SEQ ID NO: 153 |
| IgG-Fc-07 | SEQ ID NO: 7 | SEQ ID NO: 56 | SEQ ID NO: 105 | SEQ ID NO: 154 |
| IgG-Fc-08 | SEQ ID NO: 8 | SEQ ID NO: 57 | SEQ ID NO: 106 | SEQ ID NO: 155 |
| IgG-Fc-09 | SEQ ID NO: 9 | SEQ ID NO: 58 | SEQ ID NO: 107 | SEQ ID NO: 156 |
| IgG-Fc-10 | SEQ ID NO: 10 | SEQ ID NO: 59 | SEQ ID NO: 108 | SEQ ID NO: 157 |
| IgG-Fc-11 | SEQ ID NO: 11 | SEQ ID NO: 60 | SEQ ID NO: 109 | SEQ ID NO: 158 |
| IgG-Fc-12 | SEQ ID NO: 12 | SEQ ID NO: 61 | SEQ ID NO: 110 | SEQ ID NO: 159 |
| IgG-Fc-13 | SEQ ID NO: 13 | SEQ ID NO: 62 | SEQ ID NO: 111 | SEQ ID NO: 160 |
| IgG-Fc-14 | SEQ ID NO: 14 | SEQ ID NO: 63 | SEQ ID NO: 112 | SEQ ID NO: 161 |
| IgG-Fc-15 | SEQ ID NO: 15 | SEQ ID NO: 64 | SEQ ID NO: 113 | SEQ ID NO: 162 |
| IgG-Fc-16 | SEQ ID NO: 16 | SEQ ID NO: 65 | SEQ ID NO: 114 | SEQ ID NO: 163 |
| IgG-Fc-17 | SEQ ID NO: 17 | SEQ ID NO: 66 | SEQ ID NO: 115 | SEQ ID NO: 164 |
| IgG-Fc-18 | SEQ ID NO: 18 | SEQ ID NO: 67 | SEQ ID NO: 116 | SEQ ID NO: 165 |
| IgG-Fc-19 | SEQ ID NO: 19 | SEQ ID NO: 68 | SEQ ID NO: 117 | SEQ ID NO: 166 |
| IgG-Fc-20 | SEQ ID NO: 20 | SEQ ID NO: 69 | SEQ ID NO: 118 | SEQ ID NO: 167 |
| IgG-Fc-21 | SEQ ID NO: 21 | SEQ ID NO: 70 | SEQ ID NO: 119 | SEQ ID NO: 168 |
| IgG-Fc-22 | SEQ ID NO: 22 | SEQ ID NO: 71 | SEQ ID NO: 120 | SEQ ID NO: 169 |
| IgG-Fc-23 | SEQ ID NO: 23 | SEQ ID NO: 72 | SEQ ID NO: 121 | SEQ ID NO: 170 |
| IgG-Fc-24 | SEQ ID NO: 24 | SEQ ID NO: 73 | SEQ ID NO: 122 | SEQ ID NO: 171 |
| IgG-Fc-25 | SEQ ID NO: 25 | SEQ ID NO: 74 | SEQ ID NO: 123 | SEQ ID NO: 172 |
| IgG-Fc-26 | SEQ ID NO: 26 | SEQ ID NO: 75 | SEQ ID NO: 124 | SEQ ID NO: 173 |
| IgG-Fc-27 | SEQ ID NO: 27 | SEQ ID NO: 76 | SEQ ID NO: 125 | SEQ ID NO: 174 |
| IgG-Fc-28 | SEQ ID NO: 28 | SEQ ID NO: 77 | SEQ ID NO: 126 | SEQ ID NO: 175 |
| IgG-Fc-29 | SEQ ID NO: 29 | SEQ ID NO: 78 | SEQ ID NO: 127 | SEQ ID NO: 176 |
| IgG-Fc-30 | SEQ ID NO: 30 | SEQ ID NO: 79 | SEQ ID NO: 128 | SEQ ID NO: 177 |
| IgG-Fc-31 | SEQ ID NO: 31 | SEQ ID NO: 80 | SEQ ID NO: 129 | SEQ ID NO: 178 |
| IgG-Fc-32 | SEQ ID NO: 32 | SEQ ID NO: 81 | SEQ ID NO: 130 | SEQ ID NO: 179 |
| IgG-Fc-33 | SEQ ID NO: 33 | SEQ ID NO: 82 | SEQ ID NO: 131 | SEQ ID NO: 180 |
| IgG-Fc-34 | SEQ ID NO: 34 | SEQ ID NO: 83 | SEQ ID NO: 132 | SEQ ID NO: 181 |
| IgG-Fc-35 | SEQ ID NO: 35 | SEQ ID NO: 84 | SEQ ID NO: 133 | SEQ ID NO: 182 |
| IgG-Fc-36 | SEQ ID NO: 36 | SEQ ID NO: 85 | SEQ ID NO: 134 | SEQ ID NO: 183 |
| IgG-Fc-37 | SEQ ID NO: 37 | SEQ ID NO: 86 | SEQ ID NO: 135 | SEQ ID NO: 184 |
| IgG-Fc-38 | SEQ ID NO: 38 | SEQ ID NO: 87 | SEQ ID NO: 136 | SEQ ID NO: 185 |
| IgG-Fc-39 | SEQ ID NO: 39 | SEQ ID NO: 88 | SEQ ID NO: 137 | SEQ ID NO: 186 |
| IgG-Fc-40 | SEQ ID NO: 40 | SEQ ID NO: 89 | SEQ ID NO: 138 | SEQ ID NO: 187 |
| IgG-Fc-41 | SEQ ID NO: 41 | SEQ ID NO: 90 | SEQ ID NO: 139 | SEQ ID NO: 188 |
| IgG-Fc-42 | SEQ ID NO: 42 | SEQ ID NO: 91 | SEQ ID NO: 140 | SEQ ID NO: 189 |
| IgG-Fc-43 | SEQ ID NO: 43 | SEQ ID NO: 92 | SEQ ID NO: 141 | SEQ ID NO: 190 |
| IgG-Fc-44 | SEQ ID NO: 44 | SEQ ID NO: 93 | SEQ ID NO: 142 | SEQ ID NO: 191 |
| IgG-Fc-45 | SEQ ID NO: 45 | SEQ ID NO: 94 | SEQ ID NO: 143 | SEQ ID NO: 192 |
| IgG-Fc-46 | SEQ ID NO: 46 | SEQ ID NO: 95 | SEQ ID NO: 144 | SEQ ID NO: 193 |
| IgG-Fc-47 | SEQ ID NO: 47 | SEQ ID NO: 96 | SEQ ID NO: 145 | SEQ ID NO: 194 |
| IgG-Fc-48 | SEQ ID NO: 48 | SEQ ID NO: 97 | SEQ ID NO: 146 | SEQ ID NO: 195 |
| IgG-Fc-49 | SEQ ID NO: 49 | SEQ ID NO: 98 | SEQ ID NO: 147 | SEQ ID NO: 196 |

Example 1.1

Production of IgG-Fc Domain Binding VHH Fragments

The IgG-binding proteins of the invention were produced in yeast using strains and expression-constructs as described by van de Laar, et al., (2007, Biotechnology and Bioengineering, Vol. 96, No. 3: 483-494). Production of IgG-binding proteins was performed in standard bioreactors with a working volume of between 10 and 10,000 liters. Dissolved oxygen (Ingold DO2 electrode, Mettler-Toledo) was controlled by automatic adjustment of the impeller speed. The pH (Mettler-Toledo Inpro 3100 gel electrode or Broadley James F635 gel electrode) was controlled using phosphoric acid and ammoniac gas or ammonia solution. Foaming was detected by a foam level sensor (Thermo Russell) and controlled by 5-10% Struktol J673 addition. Temperature (PT100 electrode) was controlled via a cooling jacket and heating jacket. The offgas (Prima 600 mass spectrophotometer, VG gas analysis systems) analysed the ethanol concentration, rO2 and rCO2. Adding 3%-8% full-grown inoculum started the batch phase (30° C., 0.3-0.4 VVM air, DO2 minimum 30%, pH 5.0). The ethanol fermentations were automatically started when the ethanol concentration in offgas was declining in batch phase. The feed was applied according to a pulsed feed profile to maintain the ethanol level within the demanded margins. The feed phases were performed at 21° C. and 0.7-1.1 VVM air. During the ethanol fermentations the DO2 decreased to 0% and accumulated ethanol was further controlled by a pulsed feed profile. Feed phase was stopped when the ethanol feed was depleted. The broth was chilled to a temperature between 5-10° C. until further processing, including removal of spent biomass removal.

Typical fermentation parameters include a temperature of 20-31° C., a pH of 4.7-5.8, product formed: 1000-1500 mg/l cell free broth, fermentation time of 115-120 h and cell dry weight (at the end of fermentation): 95-115 g/kg.

Example 1.2

Expression Levels of IgG-Fc Domain Binding VHH Fragments in Fermentation

Expression levels of IgG-Fc binding VHH fragments in ethanol fed fermentations as described in example 1.1 were determined using a quantitative HPLC assay based on affinity chromatography columns. Samples were loaded onto an IgG coupled affinity column. After washout of unbound sample, bound IgG-Fc VHH fragment was eluted at low pH. The area of the eluted peak was determined by peak integration. Based on this peak area, the VHH fragment concentration in a sample was calculated using a standard curve.

End of Fermentation (EoF) samples at different fermentation volumes were analyzed on VHH fragment expression. An overview of VHH fragment expression levels at different fermentation volumes is presented in Table 6.

TABLE 6

Overview VHH fragment expression levels at different fermentation volumes

| VHH fragment | Batch id | Fermentation volume | Production (g/l)* |
|---|---|---|---|
| IgG-Fc-1 | 206024 | 10 m$^3$ | 1.13 |
|  | 206025 | 10 m$^3$ | 1.18 |
| IgG-Fc-10 | 204005 | 200 L | 1.35 |
|  | 206002 | 10 m$^3$ | 1.58 |
| IgG-Fc-16 | 206094 | 200 L | 3.37 |

*concentration is in g of VHH fragment per litre of supernatant at EoF

Example 2.1

ELISA and Biacore Analysis

For binding analysis in ELISA, Nunc Maxisorp binding plates were coated with antibody antigens of different species and subsequently blocked with 2% (w/v) gelatin in PBS. Bound VHH fragments were detected by either a mouse anti-His mAb in combination with a polyclonal goat-anti-mouse-HRP conjugate (Bio-Rad, 172-1011) or a polyclonal rabbit anti-llama-VHH serum in combination with a polyclonal swine-anti-rabbit IgG-HPO conjugate (Dako, P217).

Binding analysis using surface plasmon resonance analysis (SPR) were performed on a BiaCore 3000. For this purpose, antibody antigens were immobilised onto the surface of a CM5 sensor chip and subsequently incubated with anti IgG-Fc VHH fragments in HBS-EP buffer (0.01 M HEPES, pH 7.4; 0.15 M NaCl; 3 mM EDTA; 0.005% Surfactant P20). Binding was allowed for 1 minute at 5 µl/min followed by a dissociation step of 2.5 minutes at 5 µl/min. Binding signals (Resonance Units) were compared to background signals measured with HBS-EP buffer only.

No discrepancy was found between ELISA—and Biacore measurements. An overview of the specificity of the tested anti IgG-Fc VHH fragments is given in Table 7. For comparison, the relative reactivity of Protein A and G towards different IgG species is given in Table 8.

TABLE 7

Binding specificity of anti IgG-Fc VHH fragments (ELISA).

| IgG-Fc seq | IgG Fc domain species | no binding to IgG-Fc from |
|---|---|---|
| 1-49 | mammalian |  |
| 1 to 25, 31 to 36, 38, 43, 44 | human | mouse, bovine |
| 1 to 25, 33, 34, 38, 44 | human (all subclasses) | mouse, bovine, goat |
| 1 to 15 | human (all subclasses) | mouse, bovine, rat, syrian hamster, guinea pig, dog, cat, goat, sheep |
| 1 to 9 | human (all subclasses), Human IgG recovery of at least 99% (0.1 M glycine, pH 3.0) | mouse, bovine, rat, syrian hamster, guinea pig, dog, cat, goat, sheep |

TABLE 7-continued

Binding specificity of anti IgG-Fc VHH fragments (ELISA).

| IgG-Fc seq | IgG Fc domain species | no binding to IgG-Fc from |
|---|---|---|
| 10 to 15 | human (all subclasses), binding affinity at least $4 \cdot 10^9$ $M^{-1}$; expression level in yeast at least 1.2 g/l | mouse, bovine, rat, syrian hamster, guinea pig, dog, cat, goat, sheep |
| 16, 26 to 30, 37, 42, 47 to 49 | human, mouse, bovine (at least two species) | |
| 16, 28, 29, 30, 37, 42, 47 to 49 | human, bovine, mouse, rat, rabbit, dog, cat, swine, sheep, monkey (chimpanzee, rhesus), donkey, horse | |
| 16, 28, 29, 30, 48 | human, bovine, mouse, rat, rabbit, dog, cat, swine, sheep, monkey (chimpanzee, rhesus), donkey, horse, goat, syrian hamster, guinea pig | |

Anti IgG-Fc VHH fragments 36, 38-41, 43-46 show binding in ELISA to human IgG-Fc domains, however, no further analysis on other IgG species were performed.

Example 2.2

Biacore Analysis of IgG-Fc Domain Binding VHH Fragment IgG-Fc-16

Broad binding reactivity of VHH fragment IgG-Fc-16 was determined using surface plasmon resonance analysis (SPR) on a BiaCore 3000. For this purpose, purified VHH fragment IgG-Fc-16 was immobilised onto the surface of a CM5 sensor chip and subsequently incubated with purified IgG antibodies (50 μg/ml) from different species in HBS-EP buffer. Binding was allowed for 1 minute at 5 μl/min followed by a dissociation step of 2.5 minutes at 5 μl/min. Binding signals (Resonance Units) were compared to background signals measured with HBS-EP buffer only. Results are summarised in Table 8. For comparison, the relative reactivity of Protein A and G towards different IgG species is also given.

TABLE 8

Broad species reactivity of IgG-Fc domain binding VHH fragment IgG-Fc-16 in Biacore

| IgG species | Binding signal on IgG-Fc-16 (RU) | Binding reactivity of Protein A/Protein G |
|---|---|---|
| HuIgG | 1112.6 | +++/+++ |
| Human IgG, Fc fragment | 806.8 | +++/+++ |
| Human IgG, Fab fragment | −2.8 | +/+ |
| HuIgG1 | 1569.0 | +++/+++ |
| HuIgG2 | 794.7 | +++/+++ |
| HuIgG3 | 499.0 | −−/+++ |
| HuIgG4 | 710.5 | +++/+++ |
| Rat IgG | 107.7 | +/++ |
| Rat IgG1a | 431.1 | −−/+ |
| Rat IgG2a | 443.9 | −−/+++ |
| Rat IgG2b | 512.4 | −−/+ |
| Rat IgG2c | 2134.5 | ++/++ |
| Rabbit IgG | 799.6 | +++/+++ |
| Sheep IgG | 845.5 | +/++ |
| Bovine IgG | 308.8 | +/+++ |
| Bovine IgG, Fc fragment | 172.1 | |
| Bovine IgG, Fab fragment | −1.7 | |
| Mouse IgG | 468.1 | ++/++ |
| Mouse IgG 1 | 1612.6 | +/++ |
| Mouse IgG2a | 426.6 | +++/+++ |
| Dog IgG | 489.9 | +++/+ |
| Goat IgG | 257.1 | +/++ |
| Syrian Hamster IgG | 670.2 | +/++ |
| Swine IgG | 810.7 | +++/++ |
| Cat IgG | 409.5 | +++/+ |
| Donkey IgG | 637.6 | |
| Guinea IgG | 576.9 | +++/+ |
| Foetal Calf IgG | 260.0 | +/+++ |
| Newborn Calf IgG | 238.8 | +/+++ |
| Chicken IgG | −3.1 | −−/+ |
| Horse IgG | 429.6 | +/+++ |
| Buffer | −3.0 | |

+++; ++; +; −−: strong binding; moderate binding; weak binding; no binding, respectively Note that the "+" value as given in Table 8 for binding of Protein A to human IgG Fab fragments only relates to human Fab fragments comprising a VH domain belonging to the human $V_H$-III family. Observed binding reactivity of Protein G towards human IgG Fab fragments occurs through binding to an epitope present on the $C_H1$ domain of human IgG antibodies. For both Protein A and -G, however, the binding strength towards these Fab related epitopes is less compared to the epitopes present on the Fc domain of IgG antibodies. As shown in Table 8, VHH fragment IgG-Fc-16, does not co-bind to any epitope present on IgG Fab fragments.

Example 2.3

Binding Affinity Measurements on Biacore

Binding affinity constants of anti IgG-Fc VHH fragments were determined using surface plasmon resonance analysis (SPR) on a BiaCore 3000. For this purpose, purified VHH fragments were immobilised onto the surface of a CM5 sensor chip and subsequently incubated with different concentrations of purified IgG antibodies in HBS-EP buffer. Binding was allowed for 3 minutes at 30 μl/min followed by a dissociation step of 15 minutes at 30 μl/min. Binding curves were fitted according to a 1:1 Langmuir binding model using Biacore software. An overview of the calculated affinity data is given in Table 9.

TABLE 9

Biacore affinity data of anti IgG-Fc VHH fragments

| VHH | Antigen | k ass (1/Ms) | k diss (1/s) | KA (1/M) | KD (M) |
|---|---|---|---|---|---|
| IgG-Fc-1 | Human-IgG | $8.24 \times 10^4$ | $1.76 \times 10^{-4}$ | $4.67 \times 10^8$ | $2.14 \times 10^{-9}$ |
| IgG-Fc-1 | Human-IgG1 | $3.61 \times 10^5$ | $2.08 \times 10^{-4}$ | $1.74 \times 10^9$ | $5.75 \times 10^{-10}$ |
| IgG-Fc-1 | Human-IgG2 | $1.22 \times 10^5$ | $2.12 \times 10^{-4}$ | $5.76 \times 10^8$ | $1.73 \times 10^{-9}$ |
| IgG-Fc-1 | Human-IgG3 | $5.69 \times 10^3$ | $2.72 \times 10^{-4}$ | $2.09 \times 10^7$ | $4.78 \times 10^{-8}$ |
| IgG-Fc-1 | Human-IgG4 | $1.96 \times 10^5$ | $5.91 \times 10^{-5}$ | $3.32 \times 10^9$ | $3.02 \times 10^{-10}$ |
| IgG-Fc-10 | Human-IgG | $3.96 \times 10^5$ | $1.29 \times 10^{-3}$ | $3.07 \times 10^8$ | $3.25 \times 10^{-9}$ |
| IgG-Fc-10 | Human-IgG1 | $2.49 \times 10^5$ | $6.54 \times 10^{-4}$ | $3.81 \times 10^8$ | $2.62 \times 10^{-9}$ |
| IgG-Fc-10 | Human-IgG2 | $1.22 \times 10^5$ | $8.89 \times 10^{-4}$ | $1.37 \times 10^8$ | $7.29 \times 10^{-9}$ |
| IgG-Fc-10 | Human-IgG3 | $1.56 \times 10^5$ | $1.40 \times 10^{-3}$ | $1.11 \times 10^8$ | $8.99 \times 10^{-9}$ |
| IgG-Fc-10 | Human-IgG4 | $1.00 \times 10^5$ | $1.23 \times 10^{-3}$ | $8.16 \times 10^7$ | $1.23 \times 10^{-8}$ |
| IgG-Fc-16 | Human-IgG | $3.53 \times 10^4$ | $4.62 \times 10^{-4}$ | $7.65 \times 10^7$ | $1.31 \times 10^{-8}$ |
| IgG-Fc-16 | Human-IgG1 | $3.10 \times 10^4$ | $2.11 \times 10^{-4}$ | $1.47 \times 10^8$ | $6.81 \times 10^{-9}$ |
| IgG-Fc-16 | Human-IgG2 | $2.19 \times 10^4$ | $3.55 \times 10^{-4}$ | $6.17 \times 10^7$ | $1.62 \times 10^{-8}$ |
| IgG-Fc-16 | Human-IgG3 | $3.98 \times 10^4$ | $8.49 \times 10^{-4}$ | $4.69 \times 10^7$ | $2.13 \times 10^{-8}$ |
| IgG-Fc-16 | Human-IgG4 | $6.29 \times 10^4$ | $1.07 \times 10^{-4}$ | $5.89 \times 10^8$ | $1.70 \times 10^{-9}$ |
| IgG-Fc-16 | Human-IgG1 | $3.10 \times 10^4$ | $2.11 \times 10^{-4}$ | $1.47 \times 10^8$ | $6.81 \times 10^{-9}$ |
| IgG-Fc-16 | Bovine-IgG | $1.38 \times 10^5$ | $3.86 \times 10^{-4}$ | $3.59 \times 10^8$ | $2.79 \times 10^{-9}$ |
| IgG-Fc-16 | Mouse-IgG | $2.35 \times 10^4$ | $1.98 \times 10^{-4}$ | $1.19 \times 10^8$ | $8.41 \times 10^{-9}$ |

Example 3.1

Chromatography Testing

Purified anti IgG-Fc VHH fragments were dialysed to NHS coupling buffer and coupled to NHS activated sepharose 4B Fast Flow according to the suppliers protocol (GEHC) and as described in WO2006/059904. Columns were made of the coupled antibody matrix using HR 5/5 columns (GEHC). A column volume of 400 µl was used. All the chromatography experiments were performed on an Akta explorer 100. IgG samples were loaded in PBS pH 7.4, and eluted using e.g. PBS with addition of 8 M HCl to yield pH 2.1 or 0.1 M Glycine-HCl at pH 2 or 3. Protein detection was performed on line by monitoring the signal of $OD_{214}$ and $OD_{280}$. An overview of the binding analysis of the tested anti IgG-Fc sepharose carriers in chromatography are given in Table 10.

TABLE 10

Binding of IgG on anti IgG-Fc sepharose carriers in chromatography

| VHH-Sepharose carrier | Human IgG | Mouse IgG | Bovine IgG |
|---|---|---|---|
| IgG-Fc-1 | + | − | − |
| IgG-Fc-10 | + | − | − |
| IgG-Fc-15 | + | − | − |
| IgG-Fc-24 | − | + | − |
| IgG-Fc-29 | + | − | + |
| IgG-Fc-16 | + | + | + |
| IgG-Fc-48 | + | + | − |

Example 3.1

Dynamic Binding Capacities of IgG-Fc Domain Binding VHH Fragments

The dynamic binding capacity (DBC) of the IgG-Fc domain binding VHH fragments immobilized onto NHS sepharose was tested. 10 ml of 1.0 mg/ml human IgG in PBS pH 7.4 was loaded on a 400 µl column with a linear flow of 150 cm/h. After the washing with 10 column volumes PBS pH 7.4, the column was eluted with 0.1 M glycine buffer pH 3.0. Based on integration of the OD280 signal of the flow through and elution peak, the dynamic binding capacity of the column was calculated (Table 11).

TABLE 11

Dynamic binding capacity of anti-IgG-Fc sepharose carriers

| IgG-Fc binding VHH fragments | Dynamic binding capacity (mg human IgG/ml matrix) |
|---|---|
| IgG-Fc-1 | 18.2 |
| IgG-Fc-10 | 16.7 |
| IgG-Fc-16 | 11.5 |

Example 3.2

Elution Profile of IgG-Fc Domain Binding VHH Fragment IgG-Fc-1 in Chromatography Purified VHH fragment IgG-Fc-1 was dialysed to NHS coupling buffer and coupled to NHS activated sepharose 4B Fast Flow according to the suppliers protocol (GEHC) and as described in WO2006/059904. Columns were made of the coupled antibody matrix using HR 5/5 columns (GEHC). A column volume of 400 µl was used. For comparison a Protein A HiTrap column (1 ml) was used. All the chromatography experiments were performed on an Akta explorer 100. IgG samples (1 mg/ml) were loaded (10 ml on IgG-Fc-1 sepharose, 20 ml on Protein A HiTrap) in PBS pH 7 and eluted using the following types of first elution buffers:

0.2M Glycine in miliQ with different pH value's 0.1M Acetic Acid in miliQ with different pH value's 0.1M Citric Acid in miliQ with different pH value's As a second elution buffer (regeneration) PBS, pH2 was used.

After sample loading (linear flow: 150 cm/hr) and washout of unbound sample (linear flow: 150 cm/hr; volume: 10 cv), the first elution (linear flow: 300 cm/hr; volume: 30 cv) is carried out with one of the first elution buffers at a specific pH (see table 12). After re-equilibration of the column with binding buffer (linear flow: 300 cm/hr; volume 30 cv), a second elution (regeneration) is carried out with the second elution buffer (PBS, pH 2.0; linear flow: 300 cm/hr; volume 20 cv).

From the chromatograph, the two elution peaks are integrated, and the relation between the two was calculated. The data are presented in Table 12.

TABLE 12

Elution profile of VHH fragment IgG-Fc-1 in chromatography in comparison with Protein A

| pH | 0.2 M Glycine | | 0.1 M Acetic Acid | | 0.1 M Citric Acid | |
|---|---|---|---|---|---|---|
| | IgG-Fc-1 | Protein A | IgG-Fc-1 | Protein A | IgG-Fc-1 | Protein A |
| 2 | 100* | 100 | 100 | 100 | 100 | 100 |
| 3 | 100 | 100 | 99 | 99 | 99 | 99 |
| 4 | 98 | 96.5 | 85 | 72 | 92 | 84 |
| 4.5 | 87 | 56 | 62 | 42 | 75 | 63 |
| 5 | 78 | 19 | 44 | 23 | 60 | 33 |

*percentage of the first elution peak in comparison with the total peak area of the first and second elution peak.

Example 3.3

Elution Profile of IgG-Fc Domain Binding VHH Fragment IgG-Fc-16 in Chromatography Purified VHH fragment IgG-Fc-16 was dialysed to NHS coupling buffer and coupled to NHS activated sepharose 4B Fast Flow according to the suppliers protocol (GEHC) and as described in WO2006/059904. Columns were made of the coupled antibody matrix using HR 5/5 columns (GEHC). A column volume of 400 µl was used. All the chromatography experiments were performed on an Akta explorer 100. IgG samples (1 mg/ml) were loaded (10 ml on VHH Sepharose) in PBS pH7 and eluted using the following types of first elution buffers:

0.1 M Glycine in miliQ with different pH value's
0.1 M Arginine in miliQ with different pH value's As a second elution buffer (regeneration) PBS, pH2 was used.

After sample loading (linear flow: 150 cm/hr) and washout of unbound sample (linear 150 cm/hr; volume: 10 cv), the first elution (linear flow: 300 cm/hr; volume: 30 cv) is carried out with one of the first elution buffers at a specific pH (see table 13). After re-equilibration of the column with binding buffer (linear flow: 300 cm/hr; volume: 30 cv), a second elution (regeneration) is carried out with the second elution buffer (PBS, pH 2.0; linear flow: 300 cm/hr; volume 20 cv).

From the chromatograph, the two elution peaks are integrated, and the relation between the two was calculated. The data are presented in table 13.

TABLE 13

Elution profile of VHH fragment IgG-Fc-16 in chromatography

| First elution buffer | Elution (%) |
|---|---|
| 0.1 M Arginine pH 3.0 | 100* |
| 0.1 M Glycine pH 3.0 | 100 |
| 0.1 M Arginine pH 4.0 | 37 |
| 0.1 M Glycine pH 4.0 | 86 |

*percentage of the first elution peak in comparison with the total peak area of the first and second elution peak.

Example 3.4

Caustic Stability of VHH Fragment IgG-Fc-1 in Chromatography

Purified VHH fragment IgG-Fc-1 was dialysed to NHS coupling buffer and coupled to NHS activated agarose according to the suppliers protocol. Columns were made of the coupled antibody matrix using HR 5/5 columns (GEHC). 10 ml of 1.0 mg/ml human IgG in PBS pH 7.4 was loaded on a 400 µl column with a linear flow of 150 cm/h. After the washing with 10 column volumes PBS pH 7.4, the column was eluted with PBS adjusted to pH 2.1 with 8 M HCl. Based on integration of the OD280 signal of the flow through and elution peak, the dynamic binding capacity (DBC) of the column was calculated. The column was then incubated with 0.1 M or 0.2 M NaOH for 15 minutes at a linear flow of 150 cm/hr followed by equilibration with 10 column volumes of PBS pH 7.4. After each cycle the dynamic binding capacity was determined as described above. The residual DBC's after cycles with 0.1 M and 0.2 M NaOH are presented in FIG. 1.

No loss in DBC was found after more than 100 cycles with 0.1 M NaOH. When incubated with 0.2 M NaOH, a residual DBC of more than 90% was found after 40 cycles.

---

The invention claimed is:

1. An antigen-binding protein comprising an amino acid sequence that comprises 4 framework regions, FR1 to FR4, and 3 complementarity determining regions, CDR1 to CDR3, that are operably linked in the order FR1-CDR1-FR2-CDR2-FR3-CDR3-FR4, wherein:
   (a) the CDR1 has an amino acid sequence as set forth in SEQ ID NO: 1;
   (b) the CDR2 has an amino acid sequence as set forth in SEQ ID NO: 50; and,
   (c) the CDR3 is an amino acid sequence as set forth in SEQ ID NO: 99; and,
   wherein the antigen-binding protein has an amino acid sequence as set forth in SEQ ID NO 148, and wherein the antigen-binding protein specifically binds to the Fc domain of a human IgG molecule.

2. The antigen-binding protein according to claim 1, wherein the antigen binding protein has one or more properties selected from the group consisting of:
   (a) the antigen-binding protein binds the human IgG molecule with a binding affinity of at least 10-7 M as analyzed by surface plasmon resonance analysis (SPR) using polyclonal human IgG;
   (b) the antigen-binding protein has a dynamic binding capacity of at least 2 mg human IgG/ml resin, when coupled to N-hydroxysuccinimide (NHS) activated carrier at a density of 20 mg antigen-binding protein per ml NHS resin and using a flow-rate of 150 cm/h.

3. The antigen-binding protein according to claim 1, wherein the human IgG is an IgG1, IgG2, IgG3 or IgG4 molecule.

4. A multivalent antigen-binding protein comprising the amino acid sequences of at least two antigen-binding proteins according to claim 1.

5. The antigen-binding protein according to claim 1, wherein the antigen-binding protein is part of a fusion protein further comprising an amino acid sequence of a therapeutic protein or peptide.

6. An antigen-binding protein comprising an amino acid sequence that comprises 4 framework regions, FR1 to FR4, and 3 complementarity determining regions, CDR1 to CDR3, that are operably linked in the order FR1-CDR1-FR2-CDR2-FR3-CDR3-FR4, wherein:
   (i) the CDR1 has an amino acid sequence as set forth in SEQ ID NO: 1;
   (ii) the CDR2 has an amino acid sequence as set forth in SEQ ID NO: 50; and,
   (iii) the CDR3 is an amino acid sequence as set forth in SEQ ID NO: 99; and,
   wherein: FR1 comprises an amino acid selected from the group consisting of:
   (a) an amino acid having SEQ ID: 197;
   (b) an amino acid having at least 90% sequence identity with SEQ ID: 197; and/or,
   (c) the amino acid sequence of a) that has one or more amino acid substitutions as defined in Table 1;
   FR2 comprises an amino acid selected from the group consisting of:
   (d) an amino acid having SEQ ID: 198;
   (e) an amino acid having at least 90% sequence identity with SEQ ID: 198; and/or,
   (f) the amino acid sequence of d) that has one or more amino acid substitutions as defined in Table 2;
   FR3 comprises an amino acid selected from the group consisting of the amino acid sequence:
   (g) an amino acid having SEQ ID: 199;
   (h) an amino acid having at least 90% sequence identity with SEQ ID: 199; and/or,
   (i) the amino acid sequence of g) that has one or more amino acid substitutions as defined in Table 3; and,
   FR4 comprises an amino acid selected from the group consisting of:
   (j) an amino acid having SEQ ID: 200;
   (k) an amino acid having at least 90% sequence identity with SEQ ID: 200; and/or,
   l) the amino acid sequence of j) that has one or more amino acid substitutions as defined in Table 4, and wherein the antigen-binding protein specifically binds to the Fc domain of a human IgG molecule.

7. The antigen-binding protein according to claim 6, wherein the framework has at least 90% sequence identity with an amino acid sequence as set forth in SEQ ID NO:148.

8. The antigen-binding protein according to claim 6, wherein the framework has at least 95% sequence identity with an amino acid sequence as set forth in SEQ ID NO: 148.

* * * * *

SEQUENCE LISTING

<160> NUMBER OF SEQ ID NOS: 203

<210> SEQ ID NO 1
<211> LENGTH: 14
<212> TYPE: PRT
<213> ORGANISM: Camelus sp.

<400> SEQUENCE: 1

Gly Gly Thr Ser Ile Arg Ile Gly Ser Ile Asn Ala Leu Ala
1               5                   10

<210> SEQ ID NO 2
<211> LENGTH: 10
<212> TYPE: PRT
<213> ORGANISM: Camelus sp.

<400> SEQUENCE: 2

Gln Asn Ile Lys Ser Ile Asn Ala Met Ala
1               5                   10

```
<210> SEQ ID NO 3
<211> LENGTH: 10
<212> TYPE: PRT
<213> ORGANISM: Camelus sp.

<400> SEQUENCE: 3

Gly Ser Ser Ala Ser Ile Asn Ala Leu Gly
1               5                   10

<210> SEQ ID NO 4
<211> LENGTH: 10
<212> TYPE: PRT
<213> ORGANISM: Camelus sp.

<400> SEQUENCE: 4

Glu Asn Ala Arg Ser Ile Asn Val Met Gly
1               5                   10

<210> SEQ ID NO 5
<211> LENGTH: 10
<212> TYPE: PRT
<213> ORGANISM: Camelus sp.

<400> SEQUENCE: 5

Glu Asn Ile Ala Ser Ile Asn Thr Met Gly
1               5                   10

<210> SEQ ID NO 6
<211> LENGTH: 10
<212> TYPE: PRT
<213> ORGANISM: Camelus sp.

<400> SEQUENCE: 6

Glu Ser Ile Arg Ser Ile Asn Ala Met Gly
1               5                   10

<210> SEQ ID NO 7
<211> LENGTH: 10
<212> TYPE: PRT
<213> ORGANISM: Camelus sp.

<400> SEQUENCE: 7

Gly Asn Ile Gly Ser Val Asn Asp Met Ala
1               5                   10

<210> SEQ ID NO 8
<211> LENGTH: 10
<212> TYPE: PRT
<213> ORGANISM: Camelus sp.

<400> SEQUENCE: 8

Glu Ser Val Arg Ser Ile Asn Ala Met Gly
1               5                   10

<210> SEQ ID NO 9
<211> LENGTH: 10
<212> TYPE: PRT
<213> ORGANISM: Camelus sp.

<400> SEQUENCE: 9

Glu Ser Val Arg Ser Ile Asn Thr Met Gly
1               5                   10
```

```
<210> SEQ ID NO 10
<211> LENGTH: 10
<212> TYPE: PRT
<213> ORGANISM: Camelus sp.

<400> SEQUENCE: 10

Gly Leu Thr Val Asn Asp Leu Tyr Met Gly
1               5                   10

<210> SEQ ID NO 11
<211> LENGTH: 10
<212> TYPE: PRT
<213> ORGANISM: Camelus sp.

<400> SEQUENCE: 11

Gly Arg Thr Phe Ser Thr Tyr Ala Met Gly
1               5                   10

<210> SEQ ID NO 12
<211> LENGTH: 10
<212> TYPE: PRT
<213> ORGANISM: Camelus sp.

<400> SEQUENCE: 12

Gly Arg Thr Phe Ser Thr Tyr Ala Met Gly
1               5                   10

<210> SEQ ID NO 13
<211> LENGTH: 10
<212> TYPE: PRT
<213> ORGANISM: Camelus sp.

<400> SEQUENCE: 13

Gly Asp Thr Phe Ser Thr Tyr Ala Met Gly
1               5                   10

<210> SEQ ID NO 14
<211> LENGTH: 10
<212> TYPE: PRT
<213> ORGANISM: Camelus sp.

<400> SEQUENCE: 14

Gly Gly Thr Phe Glu Thr Tyr Ala Met Gly
1               5                   10

<210> SEQ ID NO 15
<211> LENGTH: 10
<212> TYPE: PRT
<213> ORGANISM: Camelus sp.

<400> SEQUENCE: 15

Gly Arg Gly Phe Ser Thr Tyr Ala Met Gly
1               5                   10

<210> SEQ ID NO 16
<211> LENGTH: 10
<212> TYPE: PRT
<213> ORGANISM: Camelus sp.

<400> SEQUENCE: 16

Gly Arg Ala Val Gly Asn Tyr Ile Ile Gly
1               5                   10
```

<210> SEQ ID NO 17
<211> LENGTH: 10
<212> TYPE: PRT
<213> ORGANISM: Camelus sp.

<400> SEQUENCE: 17

Gly Leu Thr Phe Ser Asn Tyr Ile Met Gly
1               5                   10

<210> SEQ ID NO 18
<211> LENGTH: 10
<212> TYPE: PRT
<213> ORGANISM: Camelus sp.

<400> SEQUENCE: 18

Gly Phe Thr Phe Asn Asn Tyr Ile Met Gly
1               5                   10

<210> SEQ ID NO 19
<211> LENGTH: 10
<212> TYPE: PRT
<213> ORGANISM: Camelus sp.

<400> SEQUENCE: 19

Glu Leu Thr Phe Asn Lys Tyr Ile Met Gly
1               5                   10

<210> SEQ ID NO 20
<211> LENGTH: 10
<212> TYPE: PRT
<213> ORGANISM: Camelus sp.

<400> SEQUENCE: 20

Gly Leu Thr Phe Ser Asn Tyr Ile Met Gly
1               5                   10

<210> SEQ ID NO 21
<211> LENGTH: 10
<212> TYPE: PRT
<213> ORGANISM: Camelus sp.

<400> SEQUENCE: 21

Gly Leu Thr Phe Ser Asn Tyr Ile Met Gly
1               5                   10

<210> SEQ ID NO 22
<211> LENGTH: 10
<212> TYPE: PRT
<213> ORGANISM: Camelus sp.

<400> SEQUENCE: 22

Gly Leu Thr Phe Ser Asn Tyr Ile Met Gly
1               5                   10

<210> SEQ ID NO 23
<211> LENGTH: 10
<212> TYPE: PRT
<213> ORGANISM: Camelus sp.

<400> SEQUENCE: 23

Gly Phe Thr Phe Ser Asn Tyr Ile Met Gly
1               5                   10

```
<210> SEQ ID NO 24
<211> LENGTH: 10
<212> TYPE: PRT
<213> ORGANISM: Camelus sp.

<400> SEQUENCE: 24

Gly Arg Thr Phe Gly Ile Tyr Ser Met Ala
1               5                   10

<210> SEQ ID NO 25
<211> LENGTH: 10
<212> TYPE: PRT
<213> ORGANISM: Camelus sp.

<400> SEQUENCE: 25

Gly Arg Thr Phe Gly Ile Tyr Ser Met Ala
1               5                   10

<210> SEQ ID NO 26
<211> LENGTH: 10
<212> TYPE: PRT
<213> ORGANISM: Camelus sp.

<400> SEQUENCE: 26

Gly Arg Thr Val Ser Ser Ser Ala Met Ala
1               5                   10

<210> SEQ ID NO 27
<211> LENGTH: 10
<212> TYPE: PRT
<213> ORGANISM: Camelus sp.

<400> SEQUENCE: 27

Gly Arg Thr Phe Ser Ser Tyr Ala Met Gly
1               5                   10

<210> SEQ ID NO 28
<211> LENGTH: 10
<212> TYPE: PRT
<213> ORGANISM: Camelus sp.

<400> SEQUENCE: 28

Gly Arg Thr Phe Ser Ser Gly Ala Met Gly
1               5                   10

<210> SEQ ID NO 29
<211> LENGTH: 10
<212> TYPE: PRT
<213> ORGANISM: Camelus sp.

<400> SEQUENCE: 29

Gly Arg Thr Phe Ser Ser Gly Ala Met Gly
1               5                   10

<210> SEQ ID NO 30
<211> LENGTH: 10
<212> TYPE: PRT
<213> ORGANISM: Camelus sp.

<400> SEQUENCE: 30

Gly Arg Thr Phe Ser Ser Gly Ala Met Gly
1               5                   10
```

```
<210> SEQ ID NO 31
<211> LENGTH: 10
<212> TYPE: PRT
<213> ORGANISM: Camelus sp.

<400> SEQUENCE: 31

Pro Arg Thr Phe Ser Val Tyr Ala Met Ala
1               5                   10

<210> SEQ ID NO 32
<211> LENGTH: 10
<212> TYPE: PRT
<213> ORGANISM: Camelus sp.

<400> SEQUENCE: 32

Pro Arg Thr Phe Ser Val Tyr Ala Met Ala
1               5                   10

<210> SEQ ID NO 33
<211> LENGTH: 10
<212> TYPE: PRT
<213> ORGANISM: Camelus sp.

<400> SEQUENCE: 33

Gly Arg Pro Phe Ser Arg Tyr Ala Met Gly
1               5                   10

<210> SEQ ID NO 34
<211> LENGTH: 10
<212> TYPE: PRT
<213> ORGANISM: Camelus sp.

<400> SEQUENCE: 34

Gly Arg Pro Phe Ser Arg Tyr Asn Met Gly
1               5                   10

<210> SEQ ID NO 35
<211> LENGTH: 10
<212> TYPE: PRT
<213> ORGANISM: Camelus sp.

<400> SEQUENCE: 35

Gly Ser Thr Phe Ser Asp Tyr Ala Met Gly
1               5                   10

<210> SEQ ID NO 36
<211> LENGTH: 10
<212> TYPE: PRT
<213> ORGANISM: Camelus sp.

<400> SEQUENCE: 36

Ala Arg Thr Phe Ser Gly Tyr Asn Met Gly
1               5                   10

<210> SEQ ID NO 37
<211> LENGTH: 10
<212> TYPE: PRT
<213> ORGANISM: Camelus sp.

<400> SEQUENCE: 37

Gly Arg Thr Phe Ser Asp Tyr His Met Gly
1               5                   10
```

```
<210> SEQ ID NO 38
<211> LENGTH: 10
<212> TYPE: PRT
<213> ORGANISM: Camelus sp.

<400> SEQUENCE: 38

Gly Gly Thr Phe Ser Arg Thr Ala Met Gly
1               5                   10

<210> SEQ ID NO 39
<211> LENGTH: 10
<212> TYPE: PRT
<213> ORGANISM: Camelus sp.

<400> SEQUENCE: 39

Gly Ser Ile Phe Gly Ile Asn Arg Met Gly
1               5                   10

<210> SEQ ID NO 40
<211> LENGTH: 10
<212> TYPE: PRT
<213> ORGANISM: Camelus sp.

<400> SEQUENCE: 40

Gly Arg Thr Phe Arg Ser Gly Leu Met Gly
1               5                   10

<210> SEQ ID NO 41
<211> LENGTH: 10
<212> TYPE: PRT
<213> ORGANISM: Camelus sp.

<400> SEQUENCE: 41

Gly Arg Thr Phe Ser Thr Tyr Ala Met Gly
1               5                   10

<210> SEQ ID NO 42
<211> LENGTH: 10
<212> TYPE: PRT
<213> ORGANISM: Camelus sp.

<400> SEQUENCE: 42

Gly Arg Thr Ser Trp Ile Tyr Gly Met Ala
1               5                   10

<210> SEQ ID NO 43
<211> LENGTH: 10
<212> TYPE: PRT
<213> ORGANISM: Camelus sp.

<400> SEQUENCE: 43

Gly Arg Thr Phe Ser Thr Thr Thr Met Gly
1               5                   10

<210> SEQ ID NO 44
<211> LENGTH: 10
<212> TYPE: PRT
<213> ORGANISM: Camelus sp.

<400> SEQUENCE: 44

Gly Phe Thr Phe Asp Asp Tyr Ala Ile Ser
1               5                   10
```

```
<210> SEQ ID NO 45
<211> LENGTH: 10
<212> TYPE: PRT
<213> ORGANISM: Camelus sp.

<400> SEQUENCE: 45

Gly Ser Ile Phe Ser Ile Ala Ser Met Gly
1               5                   10

<210> SEQ ID NO 46
<211> LENGTH: 10
<212> TYPE: PRT
<213> ORGANISM: Camelus sp.

<400> SEQUENCE: 46

Gly Asn Ile Gly Ser Ile Asn Ala Met Gly
1               5                   10

<210> SEQ ID NO 47
<211> LENGTH: 10
<212> TYPE: PRT
<213> ORGANISM: Camelus sp.

<400> SEQUENCE: 47

Gly Arg Thr Leu Ser Ser Tyr Ala Met Gly
1               5                   10

<210> SEQ ID NO 48
<211> LENGTH: 10
<212> TYPE: PRT
<213> ORGANISM: Camelus sp.

<400> SEQUENCE: 48

Gly Ile Ala Phe Glu Val Phe Asn Met Gly
1               5                   10

<210> SEQ ID NO 49
<211> LENGTH: 10
<212> TYPE: PRT
<213> ORGANISM: Camelus sp.

<400> SEQUENCE: 49

Gly Phe Thr Phe Ser Ser Tyr Tyr Met Ser
1               5                   10

<210> SEQ ID NO 50
<211> LENGTH: 16
<212> TYPE: PRT
<213> ORGANISM: Camelus sp.

<400> SEQUENCE: 50

Ala Val Thr Glu Gly Gly Ser Thr Asn Tyr Ala Asp Phe Val Lys Gly
1               5                   10                  15

<210> SEQ ID NO 51
<211> LENGTH: 16
<212> TYPE: PRT
<213> ORGANISM: Camelus sp.

<400> SEQUENCE: 51

Ser Ile Thr Ser Asp Gly Ser Thr Asn Tyr Ala Asp Ser Val Lys Ala
1               5                   10                  15
```

```
<210> SEQ ID NO 52
<211> LENGTH: 16
<212> TYPE: PRT
<213> ORGANISM: Camelus sp.

<400> SEQUENCE: 52

Thr Ile Thr Ser Glu Gly Thr Thr Asn Tyr Ala Asp Ser Val Lys Gly
1               5                   10                  15

<210> SEQ ID NO 53
<211> LENGTH: 16
<212> TYPE: PRT
<213> ORGANISM: Camelus sp.

<400> SEQUENCE: 53

Thr Ile Ala Glu Asp Gly Ser Thr Asn Tyr Ala Asp Ser Val Lys Gly
1               5                   10                  15

<210> SEQ ID NO 54
<211> LENGTH: 16
<212> TYPE: PRT
<213> ORGANISM: Camelus sp.

<400> SEQUENCE: 54

Glu Met Thr Glu Asp Gly Thr Ala Thr Tyr Leu Asp Ser Val Lys Ala
1               5                   10                  15

<210> SEQ ID NO 55
<211> LENGTH: 16
<212> TYPE: PRT
<213> ORGANISM: Camelus sp.

<400> SEQUENCE: 55

Thr Ile Thr Glu Gly Gly Ser Thr Asn Tyr Ala Asp Ser Val Lys Gly
1               5                   10                  15

<210> SEQ ID NO 56
<211> LENGTH: 16
<212> TYPE: PRT
<213> ORGANISM: Camelus sp.

<400> SEQUENCE: 56

Ile Ile Thr Ser Asp Gly Ser Thr Asn Ile Ala Glu Tyr Val Lys Gly
1               5                   10                  15

<210> SEQ ID NO 57
<211> LENGTH: 16
<212> TYPE: PRT
<213> ORGANISM: Camelus sp.

<400> SEQUENCE: 57

Thr Ala Thr Glu Gly Gly Ser Thr Asn Tyr Ala Asp Ser Val Lys Gly
1               5                   10                  15

<210> SEQ ID NO 58
<211> LENGTH: 16
<212> TYPE: PRT
<213> ORGANISM: Camelus sp.

<400> SEQUENCE: 58

Ala Ile Thr Glu Ser Gly Thr Thr Asn Tyr Ala Asp Ser Val Lys Gly
1               5                   10                  15
```

```
<210> SEQ ID NO 59
<211> LENGTH: 18
<212> TYPE: PRT
<213> ORGANISM: Camelus sp.

<400> SEQUENCE: 59

Arg Val Thr Pro Gly Asp Asn Thr Asp Tyr Thr Tyr Tyr Val Asp Ser
1               5                   10                  15
Val Lys

<210> SEQ ID NO 60
<211> LENGTH: 17
<212> TYPE: PRT
<213> ORGANISM: Camelus sp.

<400> SEQUENCE: 60

Ser Ala Asn Trp Lys Ser Gly Ser Thr Tyr Leu Val Asp Ser Val Lys
1               5                   10                  15
Gly

<210> SEQ ID NO 61
<211> LENGTH: 17
<212> TYPE: PRT
<213> ORGANISM: Camelus sp.

<400> SEQUENCE: 61

Ser Ile Asn Phe Lys Ser Gly Ser Ile Tyr Leu Ala Asp Ser Val Lys
1               5                   10                  15
Gly

<210> SEQ ID NO 62
<211> LENGTH: 17
<212> TYPE: PRT
<213> ORGANISM: Camelus sp.

<400> SEQUENCE: 62

Arg Ile Val Arg Gly Thr Glu Ser Thr Tyr Leu Ile Asp Ser Val Lys
1               5                   10                  15
Gly

<210> SEQ ID NO 63
<211> LENGTH: 17
<212> TYPE: PRT
<213> ORGANISM: Camelus sp.

<400> SEQUENCE: 63

Ser Thr Asn Trp Lys Ser Glu Arg Thr Tyr Val Ala Asp Ser Val Lys
1               5                   10                  15
Gly

<210> SEQ ID NO 64
<211> LENGTH: 17
<212> TYPE: PRT
<213> ORGANISM: Camelus sp.

<400> SEQUENCE: 64

Ser Ala Asn Trp Lys Ser Gly Ser Ile Tyr Val Ala Asp Ser Val Lys
1               5                   10                  15
Gly
```

```
<210> SEQ ID NO 65
<211> LENGTH: 17
<212> TYPE: PRT
<213> ORGANISM: Camelus sp.

<400> SEQUENCE: 65

Thr Thr Thr Arg Asp Gly Gly Ser Thr Phe Tyr Ala Asp Ser Val Lys
1               5                   10                  15

Gly

<210> SEQ ID NO 66
<211> LENGTH: 17
<212> TYPE: PRT
<213> ORGANISM: Camelus sp.

<400> SEQUENCE: 66

Ser Ile Gly Gly Ser Gly Thr Tyr Thr Tyr Tyr Ala Asp Ser Val Lys
1               5                   10                  15

Gly

<210> SEQ ID NO 67
<211> LENGTH: 17
<212> TYPE: PRT
<213> ORGANISM: Camelus sp.

<400> SEQUENCE: 67

Ser Ile Gly Gly Ser Gly Thr Tyr Thr Asp Tyr Ala Asp Ser Val Lys
1               5                   10                  15

Gly

<210> SEQ ID NO 68
<211> LENGTH: 17
<212> TYPE: PRT
<213> ORGANISM: Camelus sp.

<400> SEQUENCE: 68

Ser Ile Gly Gly Ser Gly Thr Tyr Thr Tyr Tyr Ala Asp Ser Val Lys
1               5                   10                  15

Gly

<210> SEQ ID NO 69
<211> LENGTH: 17
<212> TYPE: PRT
<213> ORGANISM: Camelus sp.

<400> SEQUENCE: 69

Ser Ile Gly Gly Ser Gly Thr Phe Thr Tyr Tyr Ala Asp Ser Val Lys
1               5                   10                  15

Gly

<210> SEQ ID NO 70
<211> LENGTH: 17
<212> TYPE: PRT
<213> ORGANISM: Camelus sp.

<400> SEQUENCE: 70

Ser Ile Gly Gly Ser Gly Thr Tyr Thr Tyr Tyr Ala Asp Ser Val Lys
1               5                   10                  15

Gly
```

-continued

```
<210> SEQ ID NO 71
<211> LENGTH: 17
<212> TYPE: PRT
<213> ORGANISM: Camelus sp.

<400> SEQUENCE: 71

Ser Ile Gly Gly Ser Gly Thr Tyr Thr Tyr Tyr Ala Asp Ser Val Lys
1               5                   10                  15

Gly

<210> SEQ ID NO 72
<211> LENGTH: 17
<212> TYPE: PRT
<213> ORGANISM: Camelus sp.

<400> SEQUENCE: 72

Ser Ile Gly Gly Ser Gly Thr Tyr Thr His Tyr Ala Asp Ser Val Lys
1               5                   10                  15

Gly

<210> SEQ ID NO 73
<211> LENGTH: 17
<212> TYPE: PRT
<213> ORGANISM: Camelus sp.

<400> SEQUENCE: 73

Ala Met Ser Trp Arg Gly Ile Ser Thr Ser Tyr Ala Asp Ser Val Lys
1               5                   10                  15

Gly

<210> SEQ ID NO 74
<211> LENGTH: 17
<212> TYPE: PRT
<213> ORGANISM: Camelus sp.

<400> SEQUENCE: 74

Ala Met Asn Trp Arg Gly Ile Ser Thr Ser Tyr Ala Asp Ser Met Lys
1               5                   10                  15

Gly

<210> SEQ ID NO 75
<211> LENGTH: 17
<212> TYPE: PRT
<213> ORGANISM: Camelus sp.

<400> SEQUENCE: 75

Ala Ile Ser Trp Ser Gly Gly Ser Tyr Tyr Ile Asp Ser Val Lys
1               5                   10                  15

Gly

<210> SEQ ID NO 76
<211> LENGTH: 17
<212> TYPE: PRT
<213> ORGANISM: Camelus sp.

<400> SEQUENCE: 76

Ala Ile Gly Trp Asn Ile Gly Asn Thr Tyr Tyr Ala Asp Ser Val Lys
1               5                   10                  15

Gly
```

```
<210> SEQ ID NO 77
<211> LENGTH: 17
<212> TYPE: PRT
<213> ORGANISM: Camelus sp.

<400> SEQUENCE: 77

Ala Ile Asn Trp Ser Val Gly Ser Thr Tyr Tyr Ala Asp Ser Val Lys
1               5                   10                  15

Asp

<210> SEQ ID NO 78
<211> LENGTH: 17
<212> TYPE: PRT
<213> ORGANISM: Camelus sp.

<400> SEQUENCE: 78

Ala Ile Asn Trp Ser Val Gly Ser Thr Tyr Tyr Ala Asp Ala Val Lys
1               5                   10                  15

Asp

<210> SEQ ID NO 79
<211> LENGTH: 17
<212> TYPE: PRT
<213> ORGANISM: Camelus sp.

<400> SEQUENCE: 79

Ala Ile Asn Trp Asn Ile Gly Asn Thr Tyr Tyr Ala Asp Ser Val Lys
1               5                   10                  15

Asp

<210> SEQ ID NO 80
<211> LENGTH: 17
<212> TYPE: PRT
<213> ORGANISM: Camelus sp.

<400> SEQUENCE: 80

His Ile Ile Trp Asp Thr Gly Phe Thr Tyr Tyr Gly Asp Ser Val Lys
1               5                   10                  15

Gly

<210> SEQ ID NO 81
<211> LENGTH: 17
<212> TYPE: PRT
<213> ORGANISM: Camelus sp.

<400> SEQUENCE: 81

Ser Ile Ile Trp Glu Thr Gly Tyr Thr Tyr Tyr Gly Asp Ser Val Lys
1               5                   10                  15

Gly

<210> SEQ ID NO 82
<211> LENGTH: 16
<212> TYPE: PRT
<213> ORGANISM: Camelus sp.

<400> SEQUENCE: 82

Ala Lys Pro Trp Ser Ala Asn Ala Glu Tyr Ala Asp Ser Val Lys Gly
1               5                   10                  15
```

```
<210> SEQ ID NO 83
<211> LENGTH: 16
<212> TYPE: PRT
<213> ORGANISM: Camelus sp.

<400> SEQUENCE: 83

Ala Lys Pro Trp Ser Ala Asn Ala Glu Tyr Ala Asp Ser Val Lys Gly
1               5                   10                  15

<210> SEQ ID NO 84
<211> LENGTH: 17
<212> TYPE: PRT
<213> ORGANISM: Camelus sp.

<400> SEQUENCE: 84

Ala Ile Ser Trp Ser Gly Gly Thr Thr Tyr Tyr Thr Gly Ser Val Lys
1               5                   10                  15

Gly

<210> SEQ ID NO 85
<211> LENGTH: 17
<212> TYPE: PRT
<213> ORGANISM: Camelus sp.

<400> SEQUENCE: 85

Ala Ile Thr Ser Asn Thr Gly Asn Thr Tyr Tyr Ala Asp Ser Val Lys
1               5                   10                  15

Gly

<210> SEQ ID NO 86
<211> LENGTH: 17
<212> TYPE: PRT
<213> ORGANISM: Camelus sp.

<400> SEQUENCE: 86

Ala Ile Thr Trp Asn Gly Gly Asp Thr Val Phe Glu Asp Ser Val Lys
1               5                   10                  15

Gly

<210> SEQ ID NO 87
<211> LENGTH: 17
<212> TYPE: PRT
<213> ORGANISM: Camelus sp.

<400> SEQUENCE: 87

Val Ile Ser Trp Gly Gly Ser Ser Thr Tyr Tyr Gly Asp Ser Val Lys
1               5                   10                  15

Gly

<210> SEQ ID NO 88
<211> LENGTH: 16
<212> TYPE: PRT
<213> ORGANISM: Camelus sp.

<400> SEQUENCE: 88

Thr Ile Thr Arg Gly Gly Asn Thr Asn Tyr Ala Asp Ser Val Glu Gly
1               5                   10                  15

<210> SEQ ID NO 89
<211> LENGTH: 17
<212> TYPE: PRT
<213> ORGANISM: Camelus sp.
```

```
<400> SEQUENCE: 89

Leu Leu Thr Trp Ser Gly Thr Tyr Thr Tyr Tyr Ala Asp Ser Val Lys
1               5                   10                  15

Gly

<210> SEQ ID NO 90
<211> LENGTH: 17
<212> TYPE: PRT
<213> ORGANISM: Camelus sp.

<400> SEQUENCE: 90

Val Ile Asn Asn Asn Gly Asp Asn Thr Tyr Tyr Thr Pro Ser Val Arg
1               5                   10                  15

Gly

<210> SEQ ID NO 91
<211> LENGTH: 16
<212> TYPE: PRT
<213> ORGANISM: Camelus sp.

<400> SEQUENCE: 91

Phe Ile Ser Ser Ser Gly Ser Pro Phe Tyr Ala Asp Ser Leu Lys Gly
1               5                   10                  15

<210> SEQ ID NO 92
<211> LENGTH: 17
<212> TYPE: PRT
<213> ORGANISM: Camelus sp.

<400> SEQUENCE: 92

Leu Ile Ser Trp Gly Gly Ser Ser Thr Asp Tyr Ala Asp Ser Val Arg
1               5                   10                  15

Gly

<210> SEQ ID NO 93
<211> LENGTH: 17
<212> TYPE: PRT
<213> ORGANISM: Camelus sp.

<400> SEQUENCE: 93

Cys Ile Thr Val Ser Asp Gly Ser Thr Tyr Asp Ala Tyr Ser Val Lys
1               5                   10                  15

Gly

<210> SEQ ID NO 94
<211> LENGTH: 16
<212> TYPE: PRT
<213> ORGANISM: Camelus sp.

<400> SEQUENCE: 94

Val Ile Gly Ser Asp Asp Asp Thr Asp Phe Gly Asp Ser Val Lys Gly
1               5                   10                  15

<210> SEQ ID NO 95
<211> LENGTH: 16
<212> TYPE: PRT
<213> ORGANISM: Camelus sp.

<400> SEQUENCE: 95

Thr Ile Thr Ser Ser Gly Thr Pro Ala Tyr Ala Asp Ser Val Lys Gly
1               5                   10                  15
```

```
<210> SEQ ID NO 96
<211> LENGTH: 17
<212> TYPE: PRT
<213> ORGANISM: Camelus sp.

<400> SEQUENCE: 96

Ala Ile Arg Arg Ser Gly Gly Ser Thr Tyr Tyr Ala Asp Ser Ala Glu
1               5                   10                  15

Gly

<210> SEQ ID NO 97
<211> LENGTH: 16
<212> TYPE: PRT
<213> ORGANISM: Camelus sp.

<400> SEQUENCE: 97

Thr Ile Thr Asn Ser Gly Ala Thr Asn Tyr Ala Asp Ser Val Lys Gly
1               5                   10                  15

<210> SEQ ID NO 98
<211> LENGTH: 17
<212> TYPE: PRT
<213> ORGANISM: Camelus sp.

<400> SEQUENCE: 98

Ser Ile Asn Thr Gly Ala Ser Ser Thr Tyr Tyr Ala Glu Ser Val Lys
1               5                   10                  15

Gly

<210> SEQ ID NO 99
<211> LENGTH: 17
<212> TYPE: PRT
<213> ORGANISM: Camelus sp.

<400> SEQUENCE: 99

Asp Lys Val Leu Tyr Ser Arg Gly Gly Tyr Tyr Ser Val Ala Asn Asp
1               5                   10                  15

Leu

<210> SEQ ID NO 100
<211> LENGTH: 16
<212> TYPE: PRT
<213> ORGANISM: Camelus sp.

<400> SEQUENCE: 100

Asp Arg Val Leu Tyr Tyr Thr Asp Arg Tyr Asp Thr Ala Asn Asp Val
1               5                   10                  15

<210> SEQ ID NO 101
<211> LENGTH: 17
<212> TYPE: PRT
<213> ORGANISM: Camelus sp.

<400> SEQUENCE: 101

Asp Lys Val Leu Tyr Asn Ser Asn Gly His Tyr Tyr Thr Ala Asn Asp
1               5                   10                  15

Tyr

<210> SEQ ID NO 102
<211> LENGTH: 17
<212> TYPE: PRT
<213> ORGANISM: Camelus sp.
```

```
<400> SEQUENCE: 102

Asp Arg Val Leu Tyr Tyr Gly Asp Leu Gly Tyr Ala Ala Gly Tyr Asp
1               5                   10                  15

Tyr

<210> SEQ ID NO 103
<211> LENGTH: 17
<212> TYPE: PRT
<213> ORGANISM: Camelus sp.

<400> SEQUENCE: 103

Asp Arg Val Leu Tyr Arg Ser Gly Gly Ile Tyr His Val Gly Ser Asn
1               5                   10                  15

Tyr

<210> SEQ ID NO 104
<211> LENGTH: 17
<212> TYPE: PRT
<213> ORGANISM: Camelus sp.

<400> SEQUENCE: 104

Asp Arg Val Leu Tyr Tyr Ser Gly Gly Thr Tyr Tyr Ser Gly Thr Asp
1               5                   10                  15

Tyr

<210> SEQ ID NO 105
<211> LENGTH: 17
<212> TYPE: PRT
<213> ORGANISM: Camelus sp.

<400> SEQUENCE: 105

Asp Arg Val Leu Tyr Lys Ser Gly Gly Thr Tyr Tyr Thr Gly Asn Asn
1               5                   10                  15

Tyr

<210> SEQ ID NO 106
<211> LENGTH: 17
<212> TYPE: PRT
<213> ORGANISM: Camelus sp.

<400> SEQUENCE: 106

Asp Arg Val Leu Tyr Tyr Ser Gly Gly Thr Tyr Tyr Ser Gly Thr Asp
1               5                   10                  15

Tyr

<210> SEQ ID NO 107
<211> LENGTH: 17
<212> TYPE: PRT
<213> ORGANISM: Camelus sp.

<400> SEQUENCE: 107

Asp Arg Val Leu Tyr Tyr Ser Ser Gly Ser Tyr His Ala Gly Asn Asp
1               5                   10                  15

Tyr

<210> SEQ ID NO 108
<211> LENGTH: 10
<212> TYPE: PRT
<213> ORGANISM: Camelus sp.
```

```
<400> SEQUENCE: 108

Arg Arg Phe Gly Ser Ser Glu Trp Asp Tyr
1               5                   10

<210> SEQ ID NO 109
<211> LENGTH: 10
<212> TYPE: PRT
<213> ORGANISM: Camelus sp.

<400> SEQUENCE: 109

Arg Ser Phe Gly Thr Gly Gln Trp Asp Tyr
1               5                   10

<210> SEQ ID NO 110
<211> LENGTH: 10
<212> TYPE: PRT
<213> ORGANISM: Camelus sp.

<400> SEQUENCE: 110

Arg Ser Phe Gly Thr Gly Gln Trp Asp Tyr
1               5                   10

<210> SEQ ID NO 111
<211> LENGTH: 10
<212> TYPE: PRT
<213> ORGANISM: Camelus sp.

<400> SEQUENCE: 111

Arg Ser Phe Gly Ala Gly Gln Trp Asp Tyr
1               5                   10

<210> SEQ ID NO 112
<211> LENGTH: 10
<212> TYPE: PRT
<213> ORGANISM: Camelus sp.

<400> SEQUENCE: 112

Arg Ser Phe Gly Thr Gly Gln Trp Asp Tyr
1               5                   10

<210> SEQ ID NO 113
<211> LENGTH: 10
<212> TYPE: PRT
<213> ORGANISM: Camelus sp.

<400> SEQUENCE: 113

Arg Ser Phe Gly Thr Gly Gln Trp Asp Tyr
1               5                   10

<210> SEQ ID NO 114
<211> LENGTH: 16
<212> TYPE: PRT
<213> ORGANISM: Camelus sp.

<400> SEQUENCE: 114

Lys Ser Trp Ser Val Pro Leu Arg Pro Thr Ser Ala Asp Phe Asp Ser
1               5                   10                  15

<210> SEQ ID NO 115
<211> LENGTH: 17
<212> TYPE: PRT
<213> ORGANISM: Camelus sp.
```

```
<400> SEQUENCE: 115

Gly Gly Arg Asp Thr Tyr Gly Tyr Ile Leu Pro Ser Arg Arg Val Asp
1               5                   10                  15

Tyr

<210> SEQ ID NO 116
<211> LENGTH: 17
<212> TYPE: PRT
<213> ORGANISM: Camelus sp.

<400> SEQUENCE: 116

Gly Gly Arg Asp Thr Tyr Gly Tyr Arg Leu Pro Thr Thr Arg Val Glu
1               5                   10                  15

Tyr

<210> SEQ ID NO 117
<211> LENGTH: 17
<212> TYPE: PRT
<213> ORGANISM: Camelus sp.

<400> SEQUENCE: 117

Gly Gly Arg Asp Thr Tyr Gly Tyr Arg Leu Pro Thr Thr Arg Val Glu
1               5                   10                  15

Phe

<210> SEQ ID NO 118
<211> LENGTH: 17
<212> TYPE: PRT
<213> ORGANISM: Camelus sp.

<400> SEQUENCE: 118

Gly Gly Arg Asp Thr Tyr Gly Tyr Lys Leu Pro Thr Thr Arg Val Asp
1               5                   10                  15

Tyr

<210> SEQ ID NO 119
<211> LENGTH: 17
<212> TYPE: PRT
<213> ORGANISM: Camelus sp.

<400> SEQUENCE: 119

Gly Gly Arg Asp Thr Tyr Gly Tyr Lys Leu Pro Thr Thr Arg Val Asp
1               5                   10                  15

Tyr

<210> SEQ ID NO 120
<211> LENGTH: 17
<212> TYPE: PRT
<213> ORGANISM: Camelus sp.

<400> SEQUENCE: 120

Gly Gly Arg Asp Thr Tyr Gly Tyr Lys Leu Pro Ser Thr Arg Val Asp
1               5                   10                  15

Tyr

<210> SEQ ID NO 121
<211> LENGTH: 17
<212> TYPE: PRT
<213> ORGANISM: Camelus sp.
```

```
<400> SEQUENCE: 121

Gly Gly Arg Ser Thr Tyr Gly Tyr Arg Leu Pro Thr Thr Arg Val Glu
1               5                   10                  15

Tyr

<210> SEQ ID NO 122
<211> LENGTH: 18
<212> TYPE: PRT
<213> ORGANISM: Camelus sp.

<400> SEQUENCE: 122

Gly Ser Asn Trp Leu Asp Pro Thr Trp Ala Gln Ser Pro Ser Asn Tyr
1               5                   10                  15

His Tyr

<210> SEQ ID NO 123
<211> LENGTH: 18
<212> TYPE: PRT
<213> ORGANISM: Camelus sp.

<400> SEQUENCE: 123

Gly Ser Ser Trp Leu Asp Pro Thr Trp Ala Gln Ser Pro Ser Asn Tyr
1               5                   10                  15

Asn Tyr

<210> SEQ ID NO 124
<211> LENGTH: 16
<212> TYPE: PRT
<213> ORGANISM: Camelus sp.

<400> SEQUENCE: 124

Asp Asp Ser Gly Ala Tyr Tyr Pro Met Glu Leu Gly Asp Phe Asp Ser
1               5                   10                  15

<210> SEQ ID NO 125
<211> LENGTH: 16
<212> TYPE: PRT
<213> ORGANISM: Camelus sp.

<400> SEQUENCE: 125

Asp Ala Ser Gly Ser Trp Tyr Pro Met Thr Val Glu Asp Tyr Asp Tyr
1               5                   10                  15

<210> SEQ ID NO 126
<211> LENGTH: 16
<212> TYPE: PRT
<213> ORGANISM: Camelus sp.

<400> SEQUENCE: 126

Asp Glu Ala Asp Gly Pro Met Ala Pro Tyr Gly Phe Arg Gly Asp Tyr
1               5                   10                  15

<210> SEQ ID NO 127
<211> LENGTH: 16
<212> TYPE: PRT
<213> ORGANISM: Camelus sp.

<400> SEQUENCE: 127

Asp Glu Ala Asp Gly Pro Met Ala Pro Tyr Gly Phe Arg Gly Asp Tyr
1               5                   10                  15
```

-continued

<210> SEQ ID NO 128
<211> LENGTH: 16
<212> TYPE: PRT
<213> ORGANISM: Camelus sp.

<400> SEQUENCE: 128

Asn Glu Ala Asp Gly Pro Met Ala Pro Tyr Gly Phe Arg Gly Asp Tyr
1               5                   10                  15

<210> SEQ ID NO 129
<211> LENGTH: 17
<212> TYPE: PRT
<213> ORGANISM: Camelus sp.

<400> SEQUENCE: 129

Lys Ser Val Gly Ser Gly Ser Val Asp Thr Leu Pro Gln Ser Tyr Asp
1               5                   10                  15

Tyr

<210> SEQ ID NO 130
<211> LENGTH: 17
<212> TYPE: PRT
<213> ORGANISM: Camelus sp.

<400> SEQUENCE: 130

Lys Arg Val Gly Ser Gly Ser Ile Ser Thr Phe Pro Gln Ser Phe Asp
1               5                   10                  15

Tyr

<210> SEQ ID NO 131
<211> LENGTH: 16
<212> TYPE: PRT
<213> ORGANISM: Camelus sp.

<400> SEQUENCE: 131

Ser Ile Ala Asp Tyr Ser Thr Ser Thr Arg Glu Glu Asp Phe Gly Leu
1               5                   10                  15

<210> SEQ ID NO 132
<211> LENGTH: 16
<212> TYPE: PRT
<213> ORGANISM: Camelus sp.

<400> SEQUENCE: 132

Ser Ile Gly Asp Tyr Ser Thr Ser Thr Arg Glu Glu Asp Phe Gly Leu
1               5                   10                  15

<210> SEQ ID NO 133
<211> LENGTH: 21
<212> TYPE: PRT
<213> ORGANISM: Camelus sp.

<400> SEQUENCE: 133

Asp Ala Thr Ala Pro Thr Leu Ala Asp Leu Cys Ile Tyr Tyr Ser Gly
1               5                   10                  15

Asp Pro Val Cys Tyr
            20

<210> SEQ ID NO 134
<211> LENGTH: 19
<212> TYPE: PRT
<213> ORGANISM: Camelus sp.

<400> SEQUENCE: 134

Ala Pro Thr Trp Tyr Ser Arg Asp Tyr Tyr Thr Arg Glu Asn Gln
1               5                   10                  15

Trp Arg Tyr

<210> SEQ ID NO 135
<211> LENGTH: 19
<212> TYPE: PRT
<213> ORGANISM: Camelus sp.

<400> SEQUENCE: 135

Ser Leu Ala Val Leu Thr Arg Pro Thr Ala Pro Val Ile Ser Ser
1               5                   10                  15

Tyr Asp Tyr

<210> SEQ ID NO 136
<211> LENGTH: 16
<212> TYPE: PRT
<213> ORGANISM: Camelus sp.

<400> SEQUENCE: 136

Asp Pro Asn Arg Glu Glu Leu Leu Thr Ser Pro Ala Arg Tyr Asp Tyr
1               5                   10                  15

<210> SEQ ID NO 137
<211> LENGTH: 15
<212> TYPE: PRT
<213> ORGANISM: Camelus sp.

<400> SEQUENCE: 137

Arg Val Gly Ile Ile Tyr Asn Asp Ile Leu Pro His Arg Asp Tyr
1               5                   10                  15

<210> SEQ ID NO 138
<211> LENGTH: 14
<212> TYPE: PRT
<213> ORGANISM: Camelus sp.

<400> SEQUENCE: 138

Ser Pro Arg Leu Gly Pro Ile Thr Pro Thr Thr Phe Asp Asn
1               5                   10

<210> SEQ ID NO 139
<211> LENGTH: 14
<212> TYPE: PRT
<213> ORGANISM: Camelus sp.

<400> SEQUENCE: 139

His Phe Thr Met Arg Thr Val Val Ala Gly Thr Ala Asp Tyr
1               5                   10

<210> SEQ ID NO 140
<211> LENGTH: 14
<212> TYPE: PRT
<213> ORGANISM: Camelus sp.

<400> SEQUENCE: 140

Gly Pro Lys Thr Thr Ala Tyr Thr Ala Asp Tyr His Tyr
1               5                   10

<210> SEQ ID NO 141
<211> LENGTH: 13
<212> TYPE: PRT
<213> ORGANISM: Camelus sp.

<400> SEQUENCE: 141

Arg Arg Asp Tyr Val Leu Tyr Asn His Glu Tyr Asp Ser
1               5                   10

<210> SEQ ID NO 142
<211> LENGTH: 13
<212> TYPE: PRT
<213> ORGANISM: Camelus sp.

<400> SEQUENCE: 142

Ser Arg Ala Pro Pro His Arg Cys Tyr Gly Met Asp His
1               5                   10

<210> SEQ ID NO 143
<211> LENGTH: 12
<212> TYPE: PRT
<213> ORGANISM: Camelus sp.

<400> SEQUENCE: 143

Leu Ile Gln Ala Ser Asp Gly Gln Tyr Gly Arg Tyr
1               5                   10

<210> SEQ ID NO 144
<211> LENGTH: 11
<212> TYPE: PRT
<213> ORGANISM: Camelus sp.

<400> SEQUENCE: 144

Asp Glu Tyr Asp Ser Ser Thr Thr Tyr Thr Arg
1               5                   10

<210> SEQ ID NO 145
<211> LENGTH: 10
<212> TYPE: PRT
<213> ORGANISM: Camelus sp.

<400> SEQUENCE: 145

Gly Asp Asp Leu Val Asp Gln Tyr Asp Tyr
1               5                   10

<210> SEQ ID NO 146
<211> LENGTH: 7
<212> TYPE: PRT
<213> ORGANISM: Camelus sp.

<400> SEQUENCE: 146

Gln Asn Ser Trp Arg Asn Ile
1               5

<210> SEQ ID NO 147
<211> LENGTH: 7
<212> TYPE: PRT
<213> ORGANISM: Camelus sp.

<400> SEQUENCE: 147

Gly Arg Ser Val Met Asp Tyr
1               5

```
<210> SEQ ID NO 148
<211> LENGTH: 129
<212> TYPE: PRT
<213> ORGANISM: Camelus sp.

<400> SEQUENCE: 148

Gln Val Gln Leu Gln Glu Ser Gly Gly Gly Leu Val Gln Pro Gly Gly
1               5                   10                  15

Ser Leu Arg Leu Ser Cys Ala Ala Ser Gly Gly Thr Ser Ile Arg Ile
            20                  25                  30

Gly Ser Ile Asn Ala Leu Ala Trp Tyr Arg Gln Ala Leu Gly Asn Gln
        35                  40                  45

Arg Glu Leu Val Ala Ala Val Thr Glu Gly Gly Ser Thr Asn Tyr Ala
    50                  55                  60

Asp Phe Val Lys Gly Arg Phe Thr Ile Ser Arg Asp Asn Ala Gln Asn
65                  70                  75                  80

Met Met Tyr Leu Gln Met Asn Ser Leu Lys Pro Glu Asp Thr Ala Val
                85                  90                  95

Tyr Tyr Cys Asn Ala Asp Lys Val Leu Tyr Ser Arg Gly Gly Tyr Tyr
            100                 105                 110

Ser Val Ala Asn Asp Leu Trp Gly Gln Gly Thr Gln Val Thr Val Ser
        115                 120                 125

Ser

<210> SEQ ID NO 149
<211> LENGTH: 124
<212> TYPE: PRT
<213> ORGANISM: Camelus sp.

<400> SEQUENCE: 149

Gln Val Gln Leu Gln Glu Ser Gly Gly Gly Leu Val Gln Pro Gly Gly
1               5                   10                  15

Ser Leu Arg Leu Ser Cys Val Pro Ser Gln Asn Ile Lys Ser Ile Asn
            20                  25                  30

Ala Met Ala Trp His Arg Gln Ala Pro Gly Lys Gln Arg Glu Leu Val
        35                  40                  45

Ala Ser Ile Thr Ser Asp Gly Ser Thr Asn Tyr Ala Asp Ser Val Lys
    50                  55                  60

Ala Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Arg Val Leu Tyr Tyr Asp Arg Tyr Asp Thr Ala Asn Asp
            100                 105                 110

Val Trp Gly Gln Gly Thr Gln Val Thr Val Ser Ser
        115                 120

<210> SEQ ID NO 150
<211> LENGTH: 125
<212> TYPE: PRT
<213> ORGANISM: Camelus sp.

<400> SEQUENCE: 150

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ser Ala Ser Ile Asn
            20                  25                  30
```

Ala Leu Gly Trp Tyr Arg Gln Ala Pro Gly Lys Gln Arg Glu Leu Val
            35                  40                  45

Ala Thr Ile Thr Ser Glu Gly Thr Thr Asn Tyr Ala Asp Ser Val Lys
 50                  55                  60

Gly Arg Phe Thr Ile Ser Arg Asp Asn Val Lys Asn Thr Val Tyr Leu
 65                  70                  75                  80

Glu Met Asn Ser Leu Val Pro Glu Asp Thr Ala Val Tyr Tyr Cys Asn
                 85                  90                  95

Ala Asp Lys Val Leu Tyr Asn Ser Asn Gly His Tyr Tyr Thr Ala Asn
            100                 105                 110

Asp Tyr Trp Gly Gln Gly Thr Gln Val Thr Val Ser Ser
            115                 120                 125

<210> SEQ ID NO 151
<211> LENGTH: 124
<212> TYPE: PRT
<213> ORGANISM: Camelus sp.

<400> SEQUENCE: 151

Gln Val Gln Leu Gln Asp Ser Gly Gly Gly Leu Val Gln Pro Gly Gly
 1               5                  10                  15

Ser Leu Arg Leu Ser Cys Ala Ala Ser Glu Asn Ala Arg Ser Ile Asn
            20                  25                  30

Val Met Gly Trp Tyr Arg Gln Leu Pro Gly Thr Gln Arg Glu Leu Val
            35                  40                  45

Ala Thr Ile Ala Glu Asp Gly Ser Thr Asn Tyr Ala Asp Ser Val Lys
 50                  55                  60

Gly Arg Phe Thr Ile Ser Arg Asp Lys Thr Lys Asn Thr Ile Tyr Leu
 65                  70                  75                  80

Gln Met Asn Ser Leu Lys Pro Glu Asp Thr Ala Val Tyr Tyr Cys Asn
                 85                  90                  95

Ala Asp Arg Val Leu Tyr Tyr Gly Asp Leu Gly Tyr Ala Ala Gly Tyr
            100                 105                 110

Asp Tyr Trp Gly Arg Gly Thr Gln Val Thr Val Ser
            115                 120

<210> SEQ ID NO 152
<211> LENGTH: 125
<212> TYPE: PRT
<213> ORGANISM: Camelus sp.

<400> SEQUENCE: 152

Gln Val Gln Leu Gln Asp Ser Gly Gly Gly Leu Val Gln Pro Gly Gly
 1               5                  10                  15

Ser Leu Arg Leu Ser Cys Ala Ala Ser Glu Asn Ile Ala Ser Ile Asn
            20                  25                  30

Thr Met Gly Trp Tyr Arg Gln Ala Pro Gly Lys Gln Arg Glu Leu Val
            35                  40                  45

Ala Glu Met Thr Glu Asp Gly Thr Ala Thr Tyr Leu Asp Ser Val Lys
 50                  55                  60

Ala Arg Phe Thr Ile Ser Arg Asp Asn Pro Gly Asn Thr Val Tyr Leu
 65                  70                  75                  80

Gln Met His Ser Leu Lys Pro Glu Asp Thr Ala Val Tyr Tyr Cys His
                 85                  90                  95

Ala Asp Arg Val Leu Tyr Arg Ser Gly Gly Ile Tyr His Val Gly Ser
            100                 105                 110

Asn Tyr Trp Gly Gln Gly Thr Gln Val Thr Val Ser Ser
            115                 120                 125

<210> SEQ ID NO 153
<211> LENGTH: 125
<212> TYPE: PRT
<213> ORGANISM: Camelus sp.

<400> SEQUENCE: 153

Gln Val Gln Leu Gln Glu Ser Gly Gly Gly Leu Val Gln Pro Gly Gly
1               5                   10                  15

Ser Leu Arg Leu Ser Cys Ala Ala Ser Glu Ser Ile Arg Ser Ile Asn
            20                  25                  30

Ala Met Gly Trp Tyr Arg Gln Ala Pro Gly Lys Gln Arg Glu Leu Val
        35                  40                  45

Ala Thr Ile Thr Glu Gly Gly Ser Thr Asn Tyr Ala Asp Ser Val Lys
    50                  55                  60

Gly Arg Phe Thr Ile Ser Arg Asp Asn Ala Lys Asn Thr Ala Tyr Leu
65                  70                  75                  80

Gln Met Asn Ser Leu Lys Pro Glu Asp Thr Ala Val Tyr Tyr Cys Asn
                85                  90                  95

Ala Asp Arg Val Leu Tyr Tyr Ser Gly Gly Thr Tyr Tyr Ser Gly Thr
            100                 105                 110

Asp Tyr Trp Gly Gln Gly Ser Gln Val Thr Val Ser Ser
            115                 120                 125

<210> SEQ ID NO 154
<211> LENGTH: 125
<212> TYPE: PRT
<213> ORGANISM: Camelus sp.

<400> SEQUENCE: 154

Gln Val Gln Leu Gln Asp Ser Gly Gly Gly Leu Val Gln Pro Gly Gly
1               5                   10                  15

Ser Leu Arg Leu Ser Cys Ala Val Ser Gly Asn Ile Gly Ser Val Asn
            20                  25                  30

Asp Met Ala Trp Tyr Arg Gln Thr Pro Gly Lys Gln Arg Glu Leu Val
        35                  40                  45

Ala Ile Ile Thr Ser Asp Gly Ser Thr Asn Ile Ala Glu Tyr Val Lys
    50                  55                  60

Gly Arg Phe Thr Ile Ser Lys Asp Arg Ala Asn Asn Met Val Phe Leu
65                  70                  75                  80

Gln Met Asn Ser Leu Lys Pro Glu Asp Thr Ala Val Tyr Tyr Cys His
                85                  90                  95

Ile Asp Arg Val Leu Tyr Lys Ser Gly Gly Thr Tyr Tyr Thr Gly Asn
            100                 105                 110

Asn Tyr Trp Gly Gln Gly Thr Gln Val Thr Val Ser Ser
            115                 120                 125

<210> SEQ ID NO 155
<211> LENGTH: 125
<212> TYPE: PRT
<213> ORGANISM: Camelus sp.

<400> SEQUENCE: 155

Gln Val Gln Leu Gln Asp Ser Gly Gly Gly Leu Val Gln Pro Gly Gly
1               5                   10                  15

Ser Leu Arg Leu Ser Cys Ala Ala Ser Glu Ser Val Arg Ser Ile Asn
            20                  25                  30

Ala Met Gly Trp Tyr Arg Gln Ala Pro Gly Lys Gln Arg Glu Leu Val
        35                  40                  45

Ala Thr Ala Thr Glu Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Arg Val Leu Tyr Tyr Ser Gly Gly Thr Tyr Tyr Ser Gly Thr
            100                 105                 110

Asp Tyr Trp Gly Gln Gly Ser Gln Val Thr Val Ser Ser
        115                 120                 125

<210> SEQ ID NO 156
<211> LENGTH: 125
<212> TYPE: PRT
<213> ORGANISM: Camelus sp.

<400> SEQUENCE: 156

Gln Val Gln Leu Gln Glu Ser Gly Gly Gly Leu Val Gln Pro Gly Gly
1               5                   10                  15

Ser Leu Arg Leu Ser Cys Ala Ala Ser Glu Ser Val Arg Ser Ile Asn
            20                  25                  30

Thr Met Gly Trp Tyr Arg Gln Ala Pro Gly Lys Gln Arg Glu Leu Val
        35                  40                  45

Ala Ala Ile Thr Glu Ser Gly Thr Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Arg Val Leu Tyr Tyr Ser Ser Gly Ser Tyr His Ala Gly Asn
            100                 105                 110

Asp Tyr Trp Gly Gln Gly Thr Gln Val Thr Val Ser Ser
        115                 120                 125

<210> SEQ ID NO 157
<211> LENGTH: 121
<212> TYPE: PRT
<213> ORGANISM: Camelus sp.

<400> SEQUENCE: 157

Gln Val Gln Leu Gln Glu Ser Gly Gly Gly Leu Val Gln Ala Gly Asp
1               5                   10                  15

Ser Leu Arg Ile Ser Cys Arg Ala Ser Gly Leu Thr Val Asn Asp Leu
            20                  25                  30

Tyr Met Gly Trp Phe Arg Gln Ala Pro Gly Lys Glu Arg Glu Phe Val
        35                  40                  45

Gly Arg Val Thr Pro Gly Asp Asn Thr Asp Tyr Thr Tyr Tyr Val Asp
    50                  55                  60

-continued

```
Ser Val Lys Gly Arg Phe Thr Ile Ser Arg Asp Ser Ala Lys Asn Thr
 65                  70                  75                  80

Val Tyr Leu Gln Met Asn Ser Leu Lys Leu Glu Asp Thr Ala Val Tyr
                 85                  90                  95

Leu Cys Ala Gly Arg Arg Phe Gly Ser Ser Glu Trp Asp Tyr Trp Gly
            100                 105                 110

Gln Gly Thr Gln Val Thr Val Ser Ser
        115                 120
```

<210> SEQ ID NO 158
<211> LENGTH: 119
<212> TYPE: PRT
<213> ORGANISM: Camelus sp.

<400> SEQUENCE: 158

```
Gln Val Gln Leu Gln Glu Ser Gly Gly Gly Leu Val Gln Ala Gly Gly
  1               5                  10                  15

Ser Leu Arg Leu Ser Cys Ala Val Ser Gly Arg Thr Phe Ser Thr Tyr
             20                  25                  30

Ala Met Gly Trp Phe Arg Gln Ala Pro Gly Lys Glu Arg Glu Phe Val
         35                  40                  45

Gly Ser Ala Asn Trp Lys Ser Gly Ser Thr Tyr Leu Val Asp Ser Val
     50                  55                  60

Lys Gly Arg Phe Thr Ile Ser Gly Asp Asn Ala His Asp Thr Val His
 65                  70                  75                  80

Leu Gln Met Thr Ser Leu Lys Pro Glu Asp Thr Gly Val Tyr Phe Cys
                 85                  90                  95

Val Ala Arg Ser Phe Gly Thr Gly Gln Trp Asp Tyr Trp Gly Gln Gly
            100                 105                 110

Thr Gln Val Thr Val Ser Ser
        115
```

<210> SEQ ID NO 159
<211> LENGTH: 119
<212> TYPE: PRT
<213> ORGANISM: Camelus sp.

<400> SEQUENCE: 159

```
Gln Val Gln Leu Gln Glu Ser Gly Gly Gly Leu Val Gln Ala Gly Gly
  1               5                  10                  15

Ser Leu Arg Leu Ser Cys Ala Val Ser Gly Arg Thr Phe Ser Thr Tyr
             20                  25                  30

Ala Met Gly Trp Phe Arg Gln Ala Pro Gly Lys Glu Arg Glu Phe Val
         35                  40                  45

Gly Ser Ile Asn Phe Lys Ser Gly Ser Ile Tyr Leu Ala Asp Ser Val
     50                  55                  60

Lys Gly Arg Phe Thr Ile Ser Gly Asp Asn Ala Gln Asn Thr Ala Tyr
 65                  70                  75                  80

Leu Gln Met Thr Ser Leu Lys Pro Glu Asp Thr Ala Val Tyr Leu Cys
                 85                  90                  95

Val Ala Arg Ser Phe Gly Thr Gly Gln Trp Asp Tyr Trp Gly Gln Gly
            100                 105                 110

Thr Gln Val Thr Val Ser Ser
        115
```

```
<210> SEQ ID NO 160
<211> LENGTH: 119
<212> TYPE: PRT
<213> ORGANISM: Camelus sp.

<400> SEQUENCE: 160

Gln Val Gln Leu Gln Glu Ser Gly Gly Gly Leu Val Gln Ala Gly Gly
1               5                   10                  15

Ser Leu Arg Leu Ser Cys Ala Ala Ser Gly Asp Thr Phe Ser Thr Tyr
            20                  25                  30

Ala Met Gly Trp Phe Arg Gln Ala Pro Gly Lys Glu Arg Glu Phe Val
        35                  40                  45

Gly Arg Ile Val Arg Gly Thr Glu Ser Thr Tyr Leu Ile Asp Ser Val
    50                  55                  60

Lys Gly Arg Phe Ala Ile Ser Arg Asp Asn Ala Gln Asn Thr Val Tyr
65                  70                  75                  80

Leu Gln Met Thr Ser Leu Lys Pro Glu Asp Thr Ala Val Tyr Phe Cys
                85                  90                  95

Val Ala Arg Ser Phe Gly Ala Gly Gln Trp Asp Tyr Trp Gly Gln Gly
            100                 105                 110

Thr Gln Val Thr Val Ser Ser
        115

<210> SEQ ID NO 161
<211> LENGTH: 119
<212> TYPE: PRT
<213> ORGANISM: Camelus sp.

<400> SEQUENCE: 161

Gln Val Gln Leu Gln Glu Ser Gly Gly Gly Leu Val Gln Thr Gly Gly
1               5                   10                  15

Ser Leu Arg Leu Ser Cys Ser Ala Ser Gly Gly Thr Phe Glu Thr Tyr
            20                  25                  30

Ala Met Gly Trp Phe Arg Gln Ala Pro Gly Lys Glu Arg Glu Phe Val
        35                  40                  45

Gly Ser Thr Asn Trp Lys Ser Glu Arg Thr Tyr Val Ala Asp Ser Val
    50                  55                  60

Lys Gly Arg Phe Thr Ile Ser Arg Asp Asn Gly Gln Tyr Thr Ala Tyr
65                  70                  75                  80

Leu Gln Met Thr Ser Leu Lys Pro Glu Asp Thr Ala Val Tyr Phe Cys
                85                  90                  95

Val Ala Arg Ser Phe Gly Thr Gly Gln Trp Asp Tyr Trp Gly Gln Gly
            100                 105                 110

Thr Gln Val Thr Val Ser Ser
        115

<210> SEQ ID NO 162
<211> LENGTH: 119
<212> TYPE: PRT
<213> ORGANISM: Camelus sp.

<400> SEQUENCE: 162

Gln Val Gln Leu Gln Glu Ser Gly Gly Gly Leu Val Gln Ala Gly Gly
1               5                   10                  15

Ser Leu Arg Leu Ser Cys Ala Val Ser Gly Arg Gly Phe Ser Thr Tyr
            20                  25                  30

Ala Met Gly Trp Phe Arg Gln Ala Pro Gly Lys Glu Arg Glu Phe Val
        35                  40                  45
```

```
Gly Ser Ala Asn Trp Lys Ser Gly Ser Ile Tyr Val Ala Asp Ser Val
    50                  55                  60

Lys Gly Arg Phe Thr Ile Ser Asn Asp Asn Ala Gln Asn Thr Val Tyr
65                  70                  75                  80

Leu Gln Met Ser Ser Leu Lys Pro Glu Asp Thr Ala Val Tyr Tyr Cys
                85                  90                  95

Val Ala Arg Ser Phe Gly Thr Gly Gln Trp Asp Tyr Trp Gly Gln Gly
            100                 105                 110

Thr Gln Val Thr Val Ser Ser
            115

<210> SEQ ID NO 163
<211> LENGTH: 125
<212> TYPE: PRT
<213> ORGANISM: Camelus sp.

<400> SEQUENCE: 163

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Ala Val Gly Asn Tyr
            20                  25                  30

Ile Ile Gly Trp Phe Arg Gln Ala Pro Gly Lys Glu Arg Glu Phe Val
        35                  40                  45

Ala Thr Thr Thr Arg Asp Gly Gly Ser Thr Phe Tyr Ala Asp Ser Val
    50                  55                  60

Lys Gly Arg Phe Thr Ile Ser Arg Asp Asn Ala Lys Asn Thr Val Asn
65                  70                  75                  80

Leu Gln Met Asn Ser Leu Glu Pro Glu Asp Thr Ala Val Tyr Tyr Cys
                85                  90                  95

Ala Ala Lys Ser Trp Ser Val Pro Leu Arg Pro Thr Ser Ala Asp Phe
            100                 105                 110

Asp Ser Trp Gly Gln Gly Thr Gln Val Thr Val Ser Ser
            115                 120                 125

<210> SEQ ID NO 164
<211> LENGTH: 126
<212> TYPE: PRT
<213> ORGANISM: Camelus sp.

<400> SEQUENCE: 164

Gln Val Gln Leu Gln Asp Ser Gly Gly Gly Leu Val Gln Ala Gly Gly
1               5                   10                  15

Ser Leu Arg Leu Ser Cys Ala Ala Ser Gly Leu Thr Phe Ser Asn Tyr
            20                  25                  30

Ile Met Gly Trp Phe Arg Gln Ala Pro Gly Lys Glu Arg Glu Ser Leu
        35                  40                  45

Ser Ser Ile Gly Gly Ser Gly Thr Tyr Thr Tyr Ala Asp Ser Val
    50                  55                  60

Lys Gly Arg Phe Thr Val Ser Arg Asp Asn Ala Lys Asn Thr Val Tyr
65                  70                  75                  80

Leu Gln Met Asn Ser Leu Lys Pro Glu Asp Thr Gly Met Tyr Tyr Cys
                85                  90                  95

Ala Ala Gly Gly Arg Asp Thr Tyr Gly Tyr Ile Leu Pro Ser Arg Arg
            100                 105                 110

Val Asp Tyr Trp Gly Lys Gly Thr Leu Val Thr Val Ser Ser
            115                 120                 125
```

```
<210> SEQ ID NO 165
<211> LENGTH: 126
<212> TYPE: PRT
<213> ORGANISM: Camelus sp.

<400> SEQUENCE: 165

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Thr Phe Asn Asn Tyr
            20                  25                  30

Ile Met Gly Trp Phe Arg Gln Ala Pro Gly Lys Glu Arg Glu Ser Leu
        35                  40                  45

Ala Ser Ile Gly Gly Ser Gly Thr Tyr Thr Asp Tyr Ala Asp Ser Val
    50                  55                  60

Lys Gly Arg Phe Thr Val Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Ala Gly Gly Arg Asp Thr Tyr Gly Tyr Arg Leu Pro Thr Thr Arg
            100                 105                 110

Val Glu Tyr Trp Gly Lys Gly Thr Leu Val Thr Val Ser Ser
        115                 120                 125

<210> SEQ ID NO 166
<211> LENGTH: 126
<212> TYPE: PRT
<213> ORGANISM: Camelus sp.

<400> SEQUENCE: 166

Gln Val Gln Leu Gln Glu Ser Gly Gly Gly Leu Val Gln Ala Gly Gly
1               5                   10                  15

Ser Leu Arg Leu Ser Cys Ala Ala Ser Glu Leu Thr Phe Asn Lys Tyr
            20                  25                  30

Ile Met Gly Trp Phe Arg Gln Ala Pro Gly Lys Glu Arg Glu Ser Leu
        35                  40                  45

Ala Ser Ile Gly Gly Ser Gly Thr Tyr Thr Tyr Ala Asp Ser Val
    50                  55                  60

Lys Gly Arg Phe Thr Val Ser Arg Asp Asn Ala Lys Asn Thr Val Tyr
65                  70                  75                  80

Leu Gln Met Asn Ser Leu Lys Ala Glu Asp Thr Ala Ile Tyr Phe Cys
                85                  90                  95

Ala Ala Gly Gly Arg Asp Thr Tyr Gly Tyr Arg Leu Pro Thr Thr Arg
            100                 105                 110

Val Glu Phe Trp Gly Lys Gly Thr Leu Val Thr Val Ser Ser
        115                 120                 125

<210> SEQ ID NO 167
<211> LENGTH: 126
<212> TYPE: PRT
<213> ORGANISM: Camelus sp.

<400> SEQUENCE: 167

Gln Val Gln Leu Gln Glu Ser Gly Gly Gly Leu Val Gln Ala Gly Gly
1               5                   10                  15

Ser Leu Arg Leu Ser Cys Ala Ala Ser Gly Leu Thr Phe Ser Asn Tyr
            20                  25                  30

Ile Met Gly Trp Phe Arg Gln Ala Pro Gly Lys Glu Arg Glu Ser Leu
        35                  40                  45
```

```
Ala Ser Ile Gly Gly Ser Gly Thr Phe Thr Tyr Tyr Ala Asp Ser Val
 50                  55                  60

Lys Gly Arg Phe Thr Val Ser Arg Asp Asn Ala Lys Asn Thr Val Tyr
 65                  70                  75                  80

Leu Gln Met Asn Ser Leu Lys Pro Glu Asp Thr Ala Ser Tyr Tyr Cys
                 85                  90                  95

Ala Ala Gly Gly Arg Asp Thr Tyr Gly Tyr Lys Leu Pro Thr Thr Arg
            100                 105                 110

Val Asp Tyr Trp Gly Lys Gly Thr Gln Val Thr Val Ser Ser
        115                 120                 125
```

<210> SEQ ID NO 168
<211> LENGTH: 126
<212> TYPE: PRT
<213> ORGANISM: Camelus sp.

<400> SEQUENCE: 168

```
Gln Val Gln Leu Gln Glu Ser Gly Gly Gly Leu Val Gln Ala Gly Gly
 1               5                  10                  15

Ser Leu Arg Leu Ser Cys Ala Ala Ser Gly Leu Thr Phe Ser Asn Tyr
             20                  25                  30

Ile Met Gly Trp Phe Arg Gln Ala Pro Gly Lys Glu Arg Glu Ser Leu
         35                  40                  45

Ala Ser Ile Gly Gly Ser Gly Thr Tyr Thr Tyr Tyr Ala Asp Ser Val
 50                  55                  60

Lys Gly Arg Phe Thr Val Ser Arg Asp Asn Ala Lys Asn Thr Val Tyr
 65                  70                  75                  80

Leu Gln Met Asn Ser Leu Lys Pro Glu Asp Thr Ala Ser Tyr Tyr Cys
                 85                  90                  95

Ala Ala Gly Gly Arg Asp Thr Tyr Gly Tyr Lys Leu Pro Thr Thr Arg
            100                 105                 110

Val Asp Tyr Trp Gly Lys Gly Thr Leu Val Thr Val Ser Ser
        115                 120                 125
```

<210> SEQ ID NO 169
<211> LENGTH: 126
<212> TYPE: PRT
<213> ORGANISM: Camelus sp.

<400> SEQUENCE: 169

```
Gln Val Gln Leu Gln Glu Ser Gly Gly Gly Leu Val Gln Ala Gly Gly
 1               5                  10                  15

Ser Leu Arg Leu Ser Cys Ala Ala Ser Gly Leu Thr Phe Ser Asn Tyr
             20                  25                  30

Ile Met Gly Trp Phe Arg Gln Ala Pro Gly Lys Glu Arg Glu Ser Leu
         35                  40                  45

Ala Ser Ile Gly Gly Ser Gly Thr Tyr Thr Tyr Tyr Ala Asp Ser Val
 50                  55                  60

Lys Gly Arg Phe Thr Val Ser Arg Asp Asn Ala Lys Asn Thr Val Tyr
 65                  70                  75                  80

Leu Gln Met Asn Ser Leu Lys Pro Glu Asp Thr Ala Ser Tyr Tyr Cys
                 85                  90                  95

Ala Ala Gly Gly Arg Asp Thr Tyr Gly Tyr Lys Leu Pro Ser Thr Arg
            100                 105                 110

Val Asp Tyr Trp Gly Lys Gly Thr Pro Val Thr Val Ser Ser
        115                 120                 125
```

<210> SEQ ID NO 170
<211> LENGTH: 126
<212> TYPE: PRT
<213> ORGANISM: Camelus sp.

<400> SEQUENCE: 170

```
Gln Val Gln Leu Gln Glu Ser Gly Gly Gly Leu Val Gln Thr Gly Gly
1               5                   10                  15

Ser Leu Arg Leu Ser Cys Ala Ala Ser Gly Phe Thr Phe Ser Asn Tyr
            20                  25                  30

Ile Met Gly Trp Phe Arg Gln Ala Pro Gly Lys Glu Arg Glu Ser Leu
        35                  40                  45

Ala Ser Ile Gly Gly Ser Gly Thr Tyr Thr His Tyr Ala Asp Ser Val
    50                  55                  60

Lys Gly Arg Phe Thr Val Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Ala Gly Gly Arg Ser Thr Tyr Gly Tyr Arg Leu Pro Thr Thr Arg
            100                 105                 110

Val Glu Tyr Trp Gly Lys Gly Thr Leu Val Thr Val Ser Ser
        115                 120                 125
```

<210> SEQ ID NO 171
<211> LENGTH: 127
<212> TYPE: PRT
<213> ORGANISM: Camelus sp.

<400> SEQUENCE: 171

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Gly Ile Tyr
            20                  25                  30

Ser Met Ala Trp Phe Arg Gln Pro Pro Gly Lys Glu Arg Glu Phe Val
        35                  40                  45

Ala Ala Met Ser Trp Arg Gly Ile Ser Thr Ser Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Gln Pro Glu Asp Thr Ala Val Tyr Phe Cys
                85                  90                  95

Ala Ala Gly Ser Asn Trp Leu Asp Pro Thr Trp Ala Gln Ser Pro Ser
            100                 105                 110

Asn Tyr His Tyr Trp Gly Gln Gly Thr Gln Val Thr Val Ser Ser
        115                 120                 125
```

<210> SEQ ID NO 172
<211> LENGTH: 127
<212> TYPE: PRT
<213> ORGANISM: Camelus sp.

<400> SEQUENCE: 172

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Gly Ile Tyr
            20                  25                  30

Ser Met Ala Trp Phe Arg Gln Gly Pro Gly Lys Gly Arg Glu Phe Val
        35                  40                  45
```

Ala Ala Met Asn Trp Arg Gly Ile Ser Thr Ser Tyr Ala Asp Ser Met
            50                  55                  60

Lys Gly Arg Phe Thr Ile Ser Arg Asp Asn Ala Lys Asn Thr Val Tyr
 65                  70                  75                  80

Leu Gln Met Asn Ser Leu Gln Pro Glu Asp Thr Ala Val Tyr Phe Cys
                85                  90                  95

Ala Ala Gly Ser Ser Trp Leu Asp Pro Thr Trp Ala Gln Ser Pro Ser
            100                 105                 110

Asn Tyr Asn Tyr Trp Gly Gln Gly Thr Gln Val Thr Val Ser Ser
            115                 120                 125

<210> SEQ ID NO 173
<211> LENGTH: 125
<212> TYPE: PRT
<213> ORGANISM: Camelus sp.

<400> SEQUENCE: 173

Gln Val Gln Leu Gln Asp Ser Gly Gly Gly Leu Val Gln Ala Gly Gly
 1               5                  10                  15

Ser Leu Arg Leu Ser Cys Ala Ala Ser Gly Arg Thr Val Ser Ser Ser
            20                  25                  30

Ala Met Ala Trp Phe Arg Gln Ala Pro Gly Lys Glu Arg Glu Phe Val
            35                  40                  45

Ala Ala Ile Ser Trp Ser Gly Gly Ser Tyr Tyr Ile Asp Ser Val
            50                  55                  60

Lys Gly Arg Phe Thr Ile Phe Gly Asp Asn Ala Lys Thr Thr Val Tyr
 65                  70                  75                  80

Leu Gln Met Asn Asn Leu Lys Pro Glu Asp Thr Ala Val Tyr Tyr Cys
                85                  90                  95

Ala Ala Asp Ser Gly Ala Tyr Tyr Pro Met Glu Leu Gly Asp Phe
            100                 105                 110

Asp Ser Trp Gly Gln Gly Thr Gln Val Thr Val Ser Ser
            115                 120                 125

<210> SEQ ID NO 174
<211> LENGTH: 125
<212> TYPE: PRT
<213> ORGANISM: Camelus sp.

<400> SEQUENCE: 174

Gln Val Gln Leu Gln Glu Ser Gly Gly Gly Leu Val Gln Ala Gly Gly
 1               5                  10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
            35                  40                  45

Ala Ala Ile Gly Trp Asn Ile Gly Asn Thr Tyr Ala Asp Ser Val
            50                  55                  60

Lys Gly Arg Phe Thr Thr Tyr Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                85                  90                  95

Ala Ala Asp Ala Ser Gly Ser Trp Tyr Pro Met Thr Val Glu Asp Tyr
            100                 105                 110

Asp Tyr Trp Gly Gln Gly Thr Gln Val Thr Val Ser Ser
            115                 120                 125

```
<210> SEQ ID NO 175
<211> LENGTH: 125
<212> TYPE: PRT
<213> ORGANISM: Camelus sp.

<400> SEQUENCE: 175

Gln Val Gln Leu Gln Asp Ser Gly Gly Gly Leu Val Gln Ala Gly Gly
1               5                   10                  15

Ser Leu Arg Leu Ser Cys Ala Ala Ser Gly Arg Thr Phe Ser Ser Gly
            20                  25                  30

Ala Met Gly Trp Phe Arg Gln Thr Pro Gly Lys Glu Arg Glu Phe Val
        35                  40                  45

Ala Ala Ile Asn Trp Ser Val Gly Ser Thr Tyr Tyr Ala Asp Ser Val
    50                  55                  60

Lys Asp Arg Phe Thr Ile Ser Arg Asp Lys Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Glu Ala Asp Gly Pro Met Ala Pro Tyr Gly Phe Arg Gly
            100                 105                 110

Asp Tyr Trp Gly Lys Gly Thr Leu Val Thr Val Ser Ser
        115                 120                 125

<210> SEQ ID NO 176
<211> LENGTH: 125
<212> TYPE: PRT
<213> ORGANISM: Camelus sp.

<400> SEQUENCE: 176

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Gly
            20                  25                  30

Ala Met Gly Trp Phe Arg Gln Thr Pro Gly Lys Glu Arg Glu Phe Val
        35                  40                  45

Ala Ala Ile Asn Trp Ser Val Gly Ser Thr Tyr Tyr Ala Asp Ala Val
    50                  55                  60

Lys Asp Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Glu Ala Asp Gly Pro Met Ala Pro Tyr Gly Phe Arg Gly
            100                 105                 110

Asp Tyr Trp Gly Lys Gly Thr Leu Val Thr Val Ser Ser
        115                 120                 125

<210> SEQ ID NO 177
<211> LENGTH: 125
<212> TYPE: PRT
<213> ORGANISM: Camelus sp.

<400> SEQUENCE: 177

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Gly
            20                  25                  30

Ala Met Gly Trp Phe Arg Gln Thr Pro Gly Lys Glu Arg Glu Phe Val
        35                  40                  45
```

```
Ala Ala Ile Asn Trp Asn Ile Gly Asn Thr Tyr Tyr Ala Asp Ser Val
    50                  55                  60

Lys Asp Arg Phe Thr Ile Ser Arg Asp Ser Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Asn Glu Ala Asp Gly Pro Met Ala Pro Tyr Gly Phe Arg Gly
                100                 105                 110

Asp Tyr Trp Gly Lys Gly Thr Leu Val Thr Val Ser Ser
            115                 120                 125

<210> SEQ ID NO 178
<211> LENGTH: 126
<212> TYPE: PRT
<213> ORGANISM: Camelus sp.

<400> SEQUENCE: 178

Gln Val Gln Leu Gln Glu Ser Gly Gly Gly Leu Val Gln Ala Gly Gly
 1               5                  10                  15

Ser Leu Arg Leu Ala Cys Ala Val Ser Pro Arg Thr Phe Ser Val Tyr
                20                  25                  30

Ala Met Ala Trp Phe Arg Gln Ala Pro Gly Lys Glu Arg Glu Phe Val
            35                  40                  45

Ala His Ile Ile Trp Asp Thr Gly Phe Thr Tyr Tyr Gly Asp Ser Val
    50                  55                  60

Lys Gly Arg Phe Thr Ile Ser Arg Asp Tyr Ala Gly Lys Thr Thr Tyr
 65                  70                  75                  80

Leu Gln Met Asn Ser Leu Lys Pro Glu Asp Thr Ala Val Tyr Tyr Cys
                 85                  90                  95

Ala Ala Lys Ser Val Gly Ser Gly Ser Val Asp Thr Leu Pro Gln Ser
                100                 105                 110

Tyr Asp Tyr Trp Gly Gln Gly Thr Gln Val Ala Val Ser Ser
            115                 120                 125

<210> SEQ ID NO 179
<211> LENGTH: 126
<212> TYPE: PRT
<213> ORGANISM: Camelus sp.

<400> SEQUENCE: 179

Gln Val Gln Leu Gln Glu Ser Gly Gly Gly Leu Val Gln Ala Gly Gly
 1               5                  10                  15

Ser Leu Arg Leu Ala Cys Ala Ala Ser Pro Arg Thr Phe Ser Val Tyr
                20                  25                  30

Ala Met Ala Trp Phe Arg Gln Ala Pro Gly Lys Glu Arg Glu Phe Val
            35                  40                  45

Ala Ser Ile Ile Trp Glu Thr Gly Tyr Thr Tyr Tyr Gly Asp Ser Val
    50                  55                  60

Lys Gly Arg Phe Thr Ile Ser Arg Asp Asn Ala Glu Lys Thr Ala Tyr
 65                  70                  75                  80

Leu Gln Leu Asn Ser Leu Lys Pro Glu Asp Thr Ala Val Tyr Tyr Cys
                 85                  90                  95

Ala Ala Lys Arg Val Gly Ser Gly Ser Ile Ser Thr Phe Pro Gln Ser
                100                 105                 110

Phe Asp Tyr Trp Gly Gln Gly Thr Gln Val Ala Val Ser Ser
            115                 120                 125
```

-continued

```
<210> SEQ ID NO 180
<211> LENGTH: 124
<212> TYPE: PRT
<213> ORGANISM: Camelus sp.

<400> SEQUENCE: 180
```

Gln Val Gln Leu Gln Asp Ser Gly Gly Gly Leu Val Gln Ala Gly Gly
1               5                   10                  15

Ser Leu Arg Leu Ser Cys Ala Ala Ser Gly Arg Pro Phe Ser Arg Tyr
            20                  25                  30

Ala Met Gly Trp Phe Arg Gln Ala Pro Gly Lys Glu Arg Glu Phe Val
        35                  40                  45

Ala Ala Lys Pro Trp Ser Ala Asn Ala Glu Tyr Ala Asp Ser Val Lys
    50                  55                  60

Gly Arg Phe Thr Ile Ser Arg Asp Asn Ala Lys Asn Thr Val Asp Leu
65                  70                  75                  80

Gln Met Asn Ser Leu Glu Pro Glu Asp Thr Ala Val Tyr Tyr Cys Ala
                85                  90                  95

Arg Ser Ile Ala Asp Tyr Ser Thr Ser Thr Arg Glu Glu Asp Phe Gly
            100                 105                 110

Leu Trp Gly Gln Gly Thr Gln Val Thr Val Ser Ser
        115                 120

```
<210> SEQ ID NO 181
<211> LENGTH: 124
<212> TYPE: PRT
<213> ORGANISM: Camelus sp.

<400> SEQUENCE: 181
```

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Pro Phe Ser Arg Tyr
            20                  25                  30

Asn Met Gly Trp Phe Arg Gln Ala Pro Gly Lys Glu Arg Glu Phe Val
        35                  40                  45

Ala Ala Lys Pro Trp Ser Ala Asn Ala Glu Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Ile Glu Pro Glu Asp Thr Ala Val Tyr Phe Cys Ala
                85                  90                  95

Arg Ser Ile Gly Asp Tyr Ser Thr Ser Thr Arg Glu Glu Asp Phe Gly
            100                 105                 110

Leu Trp Gly Gln Gly Thr Gln Val Thr Val Ser Ser
        115                 120

```
<210> SEQ ID NO 182
<211> LENGTH: 130
<212> TYPE: PRT
<213> ORGANISM: Camelus sp.

<400> SEQUENCE: 182
```

Gln Val Gln Leu Gln Glu Ser Gly Gly Gly Leu Val Gln Ala Gly Gly
1               5                   10                  15

Ser Val Arg Leu Ser Cys Ala Ala Ser Gly Ser Thr Phe Ser Asp Tyr
            20                  25                  30

Ala Met Gly Trp Phe Arg Gln Ala Pro Gly Lys Glu Arg Glu Phe Val
        35                  40                  45

```
Ala Ala Ile Ser Trp Ser Gly Gly Thr Thr Tyr Tyr Thr Gly Ser Val
        50                  55                  60

Lys Gly Arg Phe Thr Ile Ser Arg Asp Asn Ala Lys Asn Thr Val Tyr
 65                  70                  75                  80

Leu Gln Met Asp Ser Leu Lys Pro Glu Asp Thr Ala Val Tyr Ser Cys
                 85                  90                  95

Ala Ala Asp Ala Thr Ala Pro Thr Leu Ala Asp Leu Cys Ile Tyr Tyr
             100                 105                 110

Ser Gly Asp Pro Val Cys Tyr Trp Gly Gln Gly Thr Gln Val Thr Val
         115                 120                 125

Ser Ser
    130

<210> SEQ ID NO 183
<211> LENGTH: 128
<212> TYPE: PRT
<213> ORGANISM: Camelus sp.

<400> SEQUENCE: 183

Gln Val Gln Leu Gln Glu Ser Gly Gly Gly Leu Val Gln Ala Gly Asp
 1               5                  10                  15

Ser Leu Arg Leu Ser Cys Val Asp Ser Ala Arg Thr Phe Ser Gly Tyr
             20                  25                  30

Asn Met Gly Trp Phe Arg Arg Ala Pro Gly Lys Glu Arg Glu Phe Val
         35                  40                  45

Ala Ala Ile Thr Ser Asn Thr Gly Asn Thr Tyr Tyr Ala Asp Ser Val
     50                  55                  60

Lys Gly Arg Phe Thr Ile Ser Arg Asp Asn Ala Lys Asn Thr Val Tyr
 65                  70                  75                  80

Leu Gln Leu Asp Ser Leu Lys Pro Glu Asp Thr Ala Val Tyr Phe Cys
                 85                  90                  95

Ala Ala Ala Pro Thr Trp Tyr Ser Arg Asp Tyr Tyr Tyr Thr Arg Glu
             100                 105                 110

Asn Gln Trp Arg Tyr Trp Gly Gln Gly Thr Gln Val Thr Val Ser Ser
         115                 120                 125

<210> SEQ ID NO 184
<211> LENGTH: 128
<212> TYPE: PRT
<213> ORGANISM: Camelus sp.

<400> SEQUENCE: 184

Gln Val Gln Leu Gln Glu Ser Gly Gly Gly Leu Val Gln Ala Gly Asp
 1               5                  10                  15

Ser Leu Arg Leu Ser Cys Ala Ala Leu Gly Arg Thr Phe Ser Asp Tyr
             20                  25                  30

His Met Gly Trp Phe Arg Gln Ala Pro Gly Lys Glu Arg Thr Phe Val
         35                  40                  45

Ala Ala Ile Thr Trp Asn Gly Gly Asp Thr Val Phe Glu Asp Ser Val
     50                  55                  60

Lys Gly Arg Phe Thr Ile Ser Arg Asp Asn Gly Lys Lys Thr Val Ser
 65                  70                  75                  80

Leu Gln Met Ser Ser Leu Gln Pro Glu Asp Thr Ala Val Tyr Tyr Cys
                 85                  90                  95
```

```
Ala Ala Ser Leu Ala Val Leu Thr Arg Pro Thr Ala Pro Val Ile Ser
            100                 105                 110

Ser Ser Tyr Asp Tyr Trp Gly Gln Gly Thr Gln Val Thr Val Ser Ser
            115                 120                 125

<210> SEQ ID NO 185
<211> LENGTH: 125
<212> TYPE: PRT
<213> ORGANISM: Camelus sp.

<400> SEQUENCE: 185

Gln Val Gln Leu Gln Glu Ser Gly Gly Gly Leu Val Gln Pro Gly Gly
1               5                   10                  15

Ser Leu Arg Leu Ser Cys Ala Ala Ser Gly Gly Thr Phe Ser Arg Thr
            20                  25                  30

Ala Met Gly Trp Phe Arg Gln Ala Pro Gly Ala Glu Arg Glu Phe Val
        35                  40                  45

Ala Val Ile Ser Trp Gly Gly Ser Ser Thr Tyr Tyr Gly Asp Ser Val
    50                  55                  60

Lys Gly Arg Phe Ala Ile Ser Arg Asp Asn Ala Lys Asn Met Val Tyr
65                  70                  75                  80

Leu Gln Met Asn Ser Leu Lys Val Glu Asp Thr Ala Val Tyr Tyr Cys
                85                  90                  95

Ala Ala Asp Pro Asn Arg Glu Glu Leu Leu Thr Ser Pro Ala Arg Tyr
            100                 105                 110

Asp Tyr Trp Gly Gln Gly Thr Gln Val Thr Val Ser Ser
        115                 120                 125

<210> SEQ ID NO 186
<211> LENGTH: 123
<212> TYPE: PRT
<213> ORGANISM: Camelus sp.

<400> SEQUENCE: 186

Gln Val Gln Leu Gln Asp Ser Gly Gly Gly Leu Val Gln Pro Gly Gly
1               5                   10                  15

Ser Leu Lys Leu Ser Cys Ala Ala Ser Gly Ser Ile Phe Gly Ile Asn
            20                  25                  30

Arg Met Gly Trp Tyr Arg Gln Ala Pro Gly Lys Gln Arg Glu Leu Val
        35                  40                  45

Ala Thr Ile Thr Arg Gly Gly Asn Thr Asn Tyr Ala Asp Ser Val Glu
    50                  55                  60

Gly Arg Phe Thr Ile Ser Met Asp Asn Ala Lys Asn Thr Val Tyr Leu
65                  70                  75                  80

Gln Met Asp Ser Leu Lys Pro Glu Asp Thr Ala Val Tyr Ser Cys Tyr
                85                  90                  95

Ala Arg Val Gly Ile Ile Tyr Asn Asp Ile Leu Pro His Arg Asp Tyr
            100                 105                 110

Trp Gly Gln Gly Thr Gln Val Thr Val Ser Ser
        115                 120

<210> SEQ ID NO 187
<211> LENGTH: 123
<212> TYPE: PRT
<213> ORGANISM: Camelus sp.
```

<400> SEQUENCE: 187

```
Gln Val Gln Leu Gln Glu Ser Gly Gly Gly Leu Val Gln Ala Gly Gly
1               5                   10                  15
Ser Leu Arg Leu Ser Cys Ala Ala Ser Gly Arg Thr Phe Arg Ser Gly
            20                  25                  30
Leu Met Gly Trp Phe Arg Gln Ala Pro Gly Lys Glu Arg Glu Ala Val
        35                  40                  45
Ala Leu Leu Thr Trp Ser Gly Thr Tyr Thr Tyr Tyr Ala Asp Ser Val
    50                  55                  60
Lys Gly Arg Phe Thr Ile Ser Arg Asp Asn Ala Lys Asp Ala Val Tyr
65                  70                  75                  80
Leu Gln Met Asn Ser Leu Lys Pro Glu Asp Thr Gly Val Tyr Tyr Cys
                85                  90                  95
Ala Ala Ser Pro Arg Leu Gly Pro Ile Thr Pro Thr Thr Phe Asp Asn
            100                 105                 110
Trp Arg Gln Gly Thr Gln Val Asn Val Ser Ser
        115                 120
```

<210> SEQ ID NO 188
<211> LENGTH: 123
<212> TYPE: PRT
<213> ORGANISM: Camelus sp.

<400> SEQUENCE: 188

```
Gln Val Gln Leu Gln Glu Ser Gly Gly Gly Leu Val Gln Pro Gly Gly
1               5                   10                  15
Ser Leu Arg Leu Ser Cys Ala Ala Ser Gly Arg Thr Phe Ser Thr Tyr
            20                  25                  30
Ala Met Gly Trp Phe Arg Gln Ala Pro Gly Lys Glu Arg Glu Phe Val
        35                  40                  45
Ala Val Ile Asn Asn Asn Gly Asp Asn Thr Tyr Tyr Thr Pro Ser Val
    50                  55                  60
Arg Gly Arg Phe Thr Ile Ser Arg Asp Asn Ala Lys Asp Thr Gly Tyr
65                  70                  75                  80
Leu Gln Met Asn Ser Leu Lys Pro Glu Asp Thr Ala Val Tyr Tyr Cys
                85                  90                  95
Ala Ala His Phe Thr Met Arg Thr Val Val Ala Gly Thr Ala Asp Tyr
            100                 105                 110
Trp Gly Gln Gly Thr Gln Val Thr Val Ser Ser
        115                 120
```

<210> SEQ ID NO 189
<211> LENGTH: 122
<212> TYPE: PRT
<213> ORGANISM: Camelus sp.

<400> SEQUENCE: 189

```
Gln Val Gln Leu Gln Glu Ser Gly Gly Gly Leu Val Gln Ala Gly Asp
1               5                   10                  15
Ser Leu Arg Leu Ser Cys Ala Ala Ser Gly Arg Thr Ser Trp Ile Tyr
            20                  25                  30
Gly Met Ala Trp Phe Arg Gln Ala Pro Gly Lys Glu Arg Glu Phe Val
        35                  40                  45
Ala Phe Ile Ser Ser Ser Gly Ser Pro Phe Tyr Ala Asp Ser Leu Lys
    50                  55                  60
```

Gly Arg Val Thr Val Ser Arg Asp Asn Ala Lys Asn Thr Ala Tyr Leu
65                  70                  75                  80

Val Ile Asn Ser Leu Lys Pro Glu Asp Thr Ala Val Tyr Ser Cys Ala
                85                  90                  95

Thr Gly Pro Lys Thr Thr Ala Tyr Tyr Thr Ala Asp Tyr His Tyr Trp
            100                 105                 110

Ala Gln Gly Thr Gln Val Thr Val Ser Ser
        115                 120

<210> SEQ ID NO 190
<211> LENGTH: 122
<212> TYPE: PRT
<213> ORGANISM: Camelus sp.

<400> SEQUENCE: 190

Gln Val Gln Leu Gln Glu Ser Gly Gly Gly Leu Val Gln Ala Gly Asp
1               5                   10                  15

Ser Leu Arg Leu Ser Cys Val Ala Ser Gly Arg Thr Phe Ser Thr Thr
            20                  25                  30

Thr Met Gly Trp Phe Arg Gln Ala Pro Gly Lys Glu Arg Glu Phe Val
        35                  40                  45

Gly Leu Ile Ser Trp Gly Gly Ser Ser Thr Asp Tyr Ala Asp Ser Val
    50                  55                  60

Arg Gly Arg Phe Thr Ile Phe Arg Asp Asn Thr Lys Asn Thr Val Tyr
65                  70                  75                  80

Leu Gln Met Asp Ser Leu Lys Pro Glu Asp Thr Ala Val Tyr Tyr Cys
                85                  90                  95

Ala Ala Arg Arg Asp Tyr Val Leu Tyr Asn His Glu Tyr Asp Ser Trp
            100                 105                 110

Gly Gln Gly Thr Gln Val Thr Val Ser Ser
        115                 120

<210> SEQ ID NO 191
<211> LENGTH: 122
<212> TYPE: PRT
<213> ORGANISM: Camelus sp.

<400> SEQUENCE: 191

Gln Val Gln Leu Gln Glu Ser Gly Gly Gly Leu Val Gln Ala Gly Gly
1               5                   10                  15

Ser Leu Arg Leu Ser Cys Val Ala Ser Gly Phe Thr Phe Asp Asp Tyr
            20                  25                  30

Ala Ile Ser Trp Ile Arg Gln Ala Pro Gly Lys Glu Arg Glu Gly Val
        35                  40                  45

Ser Cys Ile Thr Val Ser Asp Gly Ser Thr Tyr Asp Ala Tyr Ser Val
    50                  55                  60

Lys Gly Arg Phe Thr Ile Ser Ser Asp Asp Ala Lys Asn Thr Glu Tyr
65                  70                  75                  80

Leu Leu Met Asn Ser Leu Lys Pro Asp Asp Thr Ala Val Tyr Tyr Cys
                85                  90                  95

Ala Ala Ser Arg Ala Pro Pro His Arg Cys Tyr Gly Met Asp His Trp
            100                 105                 110

Gly Lys Gly Thr Leu Ile Thr Val Ser Ser
        115                 120

-continued

<210> SEQ ID NO 192
<211> LENGTH: 120
<212> TYPE: PRT
<213> ORGANISM: Camelus sp.

<400> SEQUENCE: 192

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ser Ile Ala
            20                  25                  30

Ser Met Gly Trp Tyr Arg Glu Ala Pro Gly Lys Gln Arg Glu Leu Val
        35                  40                  45

Ala Val Ile Gly Ser Asp Asp Thr Asp Phe Gly Ser Val Lys
    50                  55                  60

Gly Arg Phe Thr Ile Ser Arg Asp Gly Ala Lys Asn Thr Val Tyr Leu
65              70                  75                  80

Gln Met Asn Ser Leu Lys Phe Glu Asp Thr Ala Val Tyr Tyr Cys Ser
                85                  90                  95

Gly Leu Ile Gln Ala Ser Asp Gly Gln Tyr Gly Arg Tyr Trp Gly Gln
            100                 105                 110

Gly Thr Gln Val Thr Val Ser Ser
        115                 120

<210> SEQ ID NO 193
<211> LENGTH: 119
<212> TYPE: PRT
<213> ORGANISM: Camelus sp.

<400> SEQUENCE: 193

Gln Val Gln Leu Gln Glu Ser Gly Gly Gly Leu Val Gln Pro Gly Gly
1               5                   10                  15

Ser Leu Arg Leu Ser Cys Ala Ala Ser Gly Asn Ile Gly Ser Ile Asn
            20                  25                  30

Ala Met Gly Trp Phe Arg Gln Ala Pro Gly Lys Gln Arg Glu Trp Val
        35                  40                  45

Ala Thr Ile Thr Ser Ser Gly Thr Pro Ala Tyr Ala Asp Ser Val Lys
    50                  55                  60

Gly Arg Phe Ile Ile Ser Arg Glu Tyr Ala Gly Asn Thr Val Phe Leu
65              70                  75                  80

Gln Val Asn Ser Leu Lys Pro Glu Asp Thr Ala Val Tyr Tyr Cys Phe
                85                  90                  95

Ala Asp Glu Tyr Asp Ser Ser Thr Thr Tyr Thr Arg Trp Gly Pro Gly
            100                 105                 110

Thr Gln Val Thr Val Ser Ser
        115

<210> SEQ ID NO 194
<211> LENGTH: 119
<212> TYPE: PRT
<213> ORGANISM: Camelus sp.

<400> SEQUENCE: 194

Gln Val Gln Leu Gln Glu Ser Gly Gly Gly Leu Val Gln Ala Gly Asp
1               5                   10                  15

Ser Leu Arg Leu Ser Cys Ala Ala Ser Gly Arg Thr Leu Ser Ser Tyr
            20                  25                  30

Ala Met Gly Trp Phe Arg Gln Val Pro Gly Lys Gly Arg Glu Phe Val
        35                  40                  45

Ala Ala Ile Arg Arg Ser Gly Gly Ser Thr Tyr Tyr Ala Asp Ser Ala
        50                  55                  60

Glu Gly Arg Phe Thr Ile Ser Arg Asp Asn Ala Lys Asn Thr Val Tyr
 65                  70                  75                  80

Leu Gln Met Asn Asn Leu Arg Pro Glu Asp Thr Ala Val Tyr Tyr Cys
                 85                  90                  95

Ala Ala Gly Asp Asp Leu Val Asp Gln Tyr Asp Tyr Trp Gly Gln Gly
            100                 105                 110

Thr Gln Val Thr Val Ser Ser
        115

<210> SEQ ID NO 195
<211> LENGTH: 115
<212> TYPE: PRT
<213> ORGANISM: Camelus sp.

<400> SEQUENCE: 195

Gln Val Gln Leu Gln Glu Ser Gly Gly Gly Leu Val Gln Pro Gly Glu
 1               5                  10                  15

Ser Leu Arg Leu Ser Cys Ala Ala Ser Gly Ile Ala Phe Glu Val Phe
             20                  25                  30

Asn Met Gly Trp Tyr Arg Gln Ala Pro Gly Lys Gln Arg Glu Leu Val
         35                  40                  45

Ala Thr Ile Thr Asn Ser Gly Ala Thr Asn Tyr Ala Asp Ser Val Lys
     50                  55                  60

Gly Arg Phe Thr Ile Ser Arg Asp Asn Ala Lys Asp Thr Leu Tyr Leu
 65                  70                  75                  80

Gln Met Asn Ser Leu Lys Pro Glu Asp Thr Ala Val Tyr Tyr Cys Asn
                 85                  90                  95

Ala Gln Asn Ser Trp Arg Asn Ile Trp Gly Gln Gly Thr Gln Val Thr
            100                 105                 110

Val Ser Ser
        115

<210> SEQ ID NO 196
<211> LENGTH: 116
<212> TYPE: PRT
<213> ORGANISM: Camelus sp.

<400> SEQUENCE: 196

Gln Val Gln Leu Gln Glu Ser Gly Gly Gly Leu Val Gln Pro Gly Gly
 1               5                  10                  15

Ser Leu Arg Val Ser Cys Ala Ala Ser Gly Phe Thr Phe Ser Ser Tyr
             20                  25                  30

Tyr Met Ser Trp Val Arg Gln Ala Pro Gly Lys Gly Leu Glu Trp Val
         35                  40                  45

Ser Ser Ile Asn Thr Gly Ala Ser Ser Thr Tyr Ala Glu Ser Val
     50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Arg Tyr Phe Cys
                 85                  90                  95

Val Arg Gly Arg Ser Val Met Asp Tyr Trp Gly Lys Gly Thr Leu Val
            100                 105                 110

Thr Val Ser Ser
        115

```
<210> SEQ ID NO 197
<211> LENGTH: 25
<212> TYPE: PRT
<213> ORGANISM: Camelus sp

<400> SEQUENCE: 197

Gln Val Gln Leu Gln Glu Ser Gly Gly Gly Leu Val Gln Ala Gly Gly
1               5                   10                  15

Ser Leu Arg Leu Ser Cys Ala Ala Ser
            20                  25

<210> SEQ ID NO 198
<211> LENGTH: 14
<212> TYPE: PRT
<213> ORGANISM: Camelus sp.

<400> SEQUENCE: 198

Trp Phe Arg Gln Ala Pro Gly Lys Glu Arg Glu Phe Val Ala
1               5                   10

<210> SEQ ID NO 199
<211> LENGTH: 33
<212> TYPE: PRT
<213> ORGANISM: Camelus sp.

<400> SEQUENCE: 199

Gly Arg Phe Thr Ile Ser Arg Asp Asn Ala Lys Asn Thr Val Tyr Leu
1               5                   10                  15

Gln Met Asp Ser Leu Lys Pro Glu Asp Thr Ala Val Tyr Ser Cys Ala
            20                  25                  30

Ala

<210> SEQ ID NO 200
<211> LENGTH: 11
<212> TYPE: PRT
<213> ORGANISM: Camelus sp.

<400> SEQUENCE: 200

Trp Gly Gln Gly Thr Gln Val Thr Val Ser Ser
1               5                   10

<210> SEQ ID NO 201
<211> LENGTH: 5
<212> TYPE: PRT
<213> ORGANISM: Artificial
<220> FEATURE:
<223> OTHER INFORMATION: binding epitope

<400> SEQUENCE: 201

Lys Pro Arg Glu Glu
1               5

<210> SEQ ID NO 202
<211> LENGTH: 7
<212> TYPE: PRT
<213> ORGANISM: Artificial
<220> FEATURE:
<223> OTHER INFORMATION: binding epitope

<400> SEQUENCE: 202

Lys Ala Lys Gly Gln Pro Arg
1               5
```

```
<210> SEQ ID NO 203
<211> LENGTH: 9
<212> TYPE: PRT
<213> ORGANISM: Artificial
<220> FEATURE:
<223> OTHER INFORMATION: binding epitope

<400> SEQUENCE: 203

Glu Trp Glu Ser Asn Gly Gln Pro Glu
1               5
```